US012171763B2

United States Patent
Evangelista et al.

(10) Patent No.: US 12,171,763 B2
(45) Date of Patent: Dec. 24, 2024

(54) METHODS AND COMPOSITIONS COMPRISING A KRASG12C INHIBITOR AND A PD-L1 BINDING ANTAGONIST FOR TREATING LUNG CANCER

(71) Applicant: Genentech, Inc., South San Francisco, CA (US)

(72) Inventors: Marie Evangelista, San Francisco, CA (US); Mark Andrew Merchant, Redwood City, CA (US); Jennifer Lee Schutzman, Belmont, CA (US); Ting-Kun Mark Lin, Mill Valley, CA (US); Stephanie Royer Joo, San Diego, CA (US); Sandhya Vinayak Mandlekar, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 17/524,049

(22) Filed: Nov. 11, 2021

(65) Prior Publication Data
US 2022/0152029 A1 May 19, 2022

Related U.S. Application Data

(60) Provisional application No. 63/113,606, filed on Nov. 13, 2020.

(51) Int. Cl.
| | | |
|---|---|---|
| A61K 31/517 | (2006.01) | |
| A61K 9/00 | (2006.01) | |
| A61K 39/395 | (2006.01) | |
| A61P 35/00 | (2006.01) | |

(52) U.S. Cl.
CPC .......... *A61K 31/517* (2013.01); *A61K 9/0019* (2013.01); *A61K 9/0053* (2013.01); *A61K 39/3955* (2013.01); *A61P 35/00* (2018.01)

(58) Field of Classification Search
CPC .. A61K 31/517; A61K 9/0019; A61K 9/0053; A61K 39/3955
See application file for complete search history.

(56) References Cited

U.S. PATENT DOCUMENTS

| 11,236,068 B2* | 2/2022 | Malhotra | C07D 401/14 |
| 2020/0181118 A1* | 6/2020 | Malhotra | C07D 405/14 |
| 2020/0222407 A1* | 7/2020 | Lipford | A61P 35/00 |
| 2022/0152029 A1* | 5/2022 | Evangelista | A61K 39/39558 |

FOREIGN PATENT DOCUMENTS

| JP | 2020-105162 A | 7/2020 |
| WO | 2020/097537 A2 | 5/2020 |
| WO | 2020/106647 A2 | 5/2020 |
| WO | WO-2022061202 A1 * | 3/2022 |

OTHER PUBLICATIONS

Dhillon et al., Atezolizumab First-Line Combination Therapy: A Review in Metastatic Nonsquamous NSCLC, Targeted Oncology, 14 :759-768, Publication Date: Nov. 14, 2019 (Year: 2019).*
Peters et al., Phase II Trial of Atezolizumab as First-Line or Subsequent Therapy for Patients With Programmed Death-Ligand 1-Selected Advanced Non-Small-Cell Lung Cancer (BIRCH), Journal of Clinical Oncology, vol. 35, 2781-2789, Publication Date: Jun. 30, 2017 (Year: 2017).*
Santini et al., Atezolizumab for the treatment of non-small cell lung cancer, Expert Rev Clin Pharmacol., 10(9): 935-945, Publication Date: Sep. 2017 (Year: 2017).*
Khan et al., Comparative analysis of immune checkpoint inhibitors and chemotherapy in the treatment of advanced non-small cell lung cancer, Medicine, 97: 33, Publication Date: Aug. 17, 2018 (Year: 2018).*
Divarasib downloaded on Sep. 19, 2023 from: https://www.medchemexpress.com/gdc-6036.html (Year: 2023).*
Patel et al., Pharmaceutical salts: a formulation trick or a clinical conundrum, The British Journal of Cardiology, 16: 281-286, Publication Date: Nov. 2009 (Year: 2009).*
Lee et al., Clinic Blood Pressure Responses tO Two Amlodipine Salt Formulations, Adipate and Besylate, in Adult Korean Patients with Mild to Moderate Hypertension, Clinical Therapeutics, vol. 27, No. 6, 728-739, Publication Date: Jun. 2005 (Year: 2005).*
Briere, D. M. et al., "The KRAS G12C Inhibitor MRTX849 Reconditions the Tumor Immune Microenvironment and Sensitizes Tumors to Checkpoint Inhibitor Therapy" Mol. Cancer Ther. 20(6):975-985 ( 2021).
Canon, J. et al., "The clinical KRAS(G12C) inhibitor AMG 510 drives anti-tumour immunity" Nature 575:271-223 ( 2019).
Clinical Trials.gov: Amgen, "Sotorasib Activity in Subjects With Advanced Solid Tumors With KRAS p.G12C Mutation (CodeBreak 101) NCT04185883" First Posted: Dec. 4, 2019, Last Update Posted: May 5, 2022; Printed: May 19, 2022: pp. 1-18, https://clinicaltrials.gov/ct2/show/NCT04185883?recrs=ab&cond=NCT04185883&draw=2&rank=1.
Hamarsheh, S. et al., "Immune modulatory effects of oncogenic KRAS in cancer" Nat. Commun. 11:1-11 ( 2020).
International Search Report with Written Opinion for PCT/US2021/058874 mailed Apr. 11, 2022, pp. 1-15.
Hans Purkey, "Discovery of GDC-6036, a clinical stage treatment for KRAS G12C-positive cancers" AACR Annual Meeting, New Orleans, USA, pp. 18 (Apr. 8-13, 2022).

(Continued)

*Primary Examiner* — Peter J Reddig
*Assistant Examiner* — Cheng Lu
(74) *Attorney, Agent, or Firm* — Genentech, Inc.

(57) ABSTRACT

Provided herein are combination therapies (compositions) and methods and uses thereof for the treatment lung cancer, where the combination therapies comprise Compound 1 or a pharmaceutically acceptable salt thereof as described herein and a PD-L1 binding antagonist (e.g., atezolizumab).

13 Claims, 4 Drawing Sheets

Specification includes a Sequence Listing.

(56) References Cited

OTHER PUBLICATIONS

Chen, H., et al., "Small-Molecule Inhibitors Directly Targeting KRAS as Anticancer Therapeutics" ACS J Med Chem 63(23):14404-14424 (Nov. 23, 2020).
"International Preliminary Report on Patentability—PCT/US2021/058874" (Report Issuance Date: May 16, 2023; Chapter I),:pp. 1-10 (May 25, 2023).

* cited by examiner

METHODS AND COMPOSITIONS COMPRISING A KRASG12C INHIBITOR AND A PD-L1 BINDING ANTIBITOR FOR TREATING LUNG CANCER

CROSS REFERENCE TO RELATED APPLICATIONS

This application claims priority to U.S. Provisional Patent Application No. 63/113,606, filed Nov. 13, 2020, which is incorporated herein by reference in its entirety and for all purposes.

FIELD OF THE INVENTION

Provided herein are combination therapies comprising a $KRas^{G12C}$ inhibitor (e.g. Compound 1) and a PD-L1 binding antagonist (e.g., atezolizumab) and methods of using such combination therapies and a $KRas^{G12C}$ inhibitor.

SEQUENCE LISTING

This application contains a Sequence Listing, which has been submitted electronically in ASCII format and is hereby incorporated by reference in its entirety. Said ASCII copy, created on Nov. 4, 2021, is named P36528_US_1_Seq_list_ST25.txt and is 9,577 bytes in size.

BACKGROUND OF THE INVENTION

The Kirsten rat sarcoma viral oncogene homolog (KRAS) is a central component of the RAS/MAPK signal transduction pathway, an intracellular network of proteins that transmit extracellular growth factor signals to regulate cell proliferation, differentiation, and survival. Mutations in KRAS can result in alterations at several amino acids, including glycine 12 (G12), glycine 13, and glutamine 61, commonly found in solid tumors and associated with tumorigenesis and aggressive tumor growth (Der et al. Proc Natl Acad Sci USA 1982; 79:3637-40; Parada et al. Nature 1982; 297:474-8; Santos et al. Nature 1982; 298:343-7; Taparowsky et al. Nature 1982; 300:762-5; Capon et al. Nature 1983; 304: 507-13). Oncogenic KRAS mutations that result in the change from G12 to cysteine (G12C) are prevalent in non-small cell lung cancer (NSCLC) (~12%), colorectal cancer (CRC) (~4%), and other tumor types 4%) (Bailey et al. Nature 2016; 531:47-52; Campbell et al. Nat Genet 2016; 48:607-16; Giannakis et al. Cell Reports 2016; 15:857-65; Hartmaier et al. Genome Med 2017; 9(16); Jordan et al. Cancer Discov 2017; 7:596-609).

Advanced stage tumors harboring the $KRas^{G12C}$ mutation (hereafter referred to as $KRas^{G12C}$-positive tumors), including NSCLC, CRC, and other solid tumors, are incurable and carry a poor prognosis (Roman et al. 2018; Wan et al. 2019). In addition, patients with advanced stage $KRas^{G12C}$-positive cancers may derive limited benefit from select chemotherapies and targeted therapies, thus, restricting effective available treatment options (Roman et al. 2018).

Thus, there is a need for effective therapies and combination therapies for treating cancers such as NSCLC harboring $KRas^{G12C}$ mutations.

SUMMARY OF THE INVENTION

Provided herein are solutions to these and other problems in the art.

In one aspect provided herein is a combination therapy comprising Compound 1 or a pharmaceutically acceptable salt thereof as described herein and a PD-L1 binding antagonist as described herein.

In one such embodiment, the anti-PD-L1 antibody is atezolizumab. In another such embodiment, Compound 1 is an adipate salt thereof. In another such embodiment, Compound 1 or a pharmaceutically acceptable salt thereof is administered QD on days 1-21 of a first 21-day cycle and atezolizumab administered Q3W on day 1 of the first 21-day cycle. In still another embodiment, Compound 1 or a pharmaceutically acceptable salt thereof is administered QD at an amount of about 50 mg-500 mg on days 1-21 of a first 21-day cycle and atezolizumab is administered Q3W at an amount of about 1200 mg on day 1 of the first 21-day cycle.

In another aspect provided herein is a method of treating lung cancer mediated by a $KRas^{G12C}$ mutation in a patient having such a lung cancer, the method comprising administering an effective amount of a combination therapy comprising Compound 1 or a pharmaceutically acceptable salt thereof as described herein and a PD-L1 binding antagonist as described herein.

In another aspect provided herein is a method of treating NSCLC comprising a $KRas^{G12C}$ mutation in a patient having such a cancer, the method comprising administering to the patient an effective amount of a combination therapy comprising: (a) Compound 1 or a pharmaceutically acceptable salt thereof, wherein Compound 1 or a pharmaceutically acceptable salt thereof QD on days 1-21 of a first 21-day cycle and; (b) atezolizumab administered Q3W on day 1 of the first 21-day cycle.

In another aspect provided herein is a method of treating NSCLC in a patient having NSCLC, the method comprising administering to the patient a treatment regimen comprising an effective amount of Compound 1 or a pharmaceutically acceptable salt thereof and a PD-L1 binding antagonist.

In another aspect provided herein is a use (U1) of a combination therapy comprising Compound 1 or a pharmaceutically acceptable salt thereof and atezolizumab for the treatment of lung cancer as described herein.

In another aspect provided herein is a use (U5) of a combination therapy comprising Compound 1 or a pharmaceutically acceptable salt thereof and atezolizumab for the manufacture of a medicament for the treatment of lung cancer.

DETAILED DESCRIPTION OF THE INVENTION

Definitions

Figure 1A:
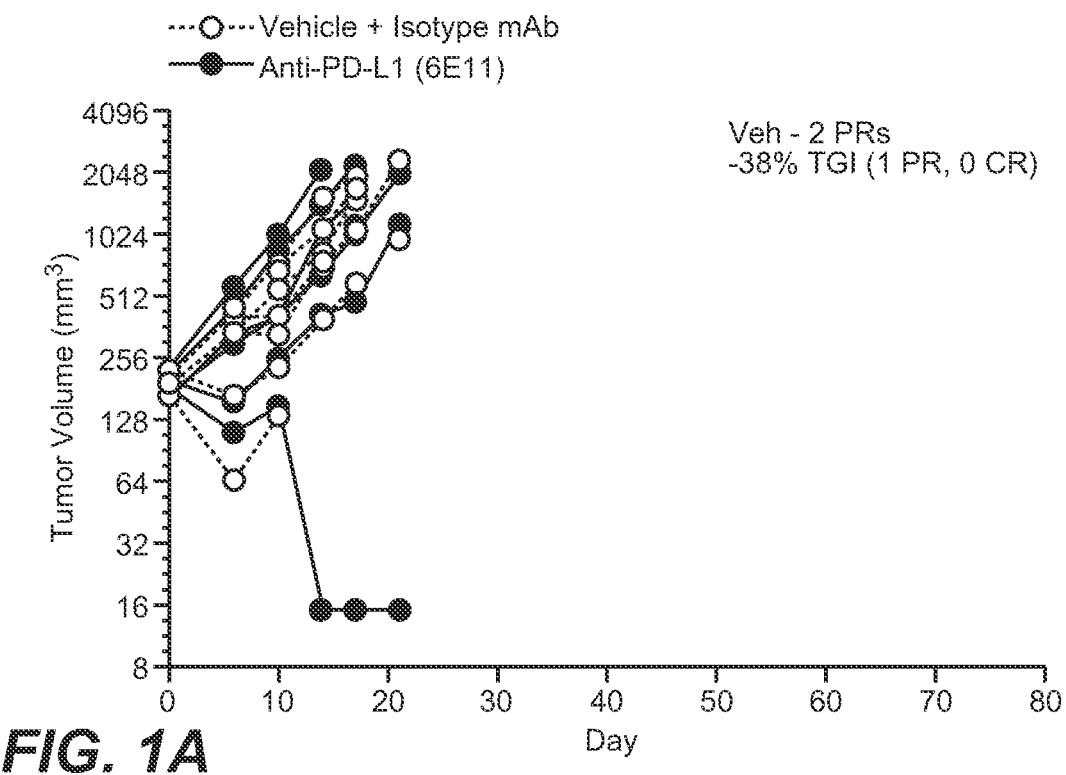
FIG. 1A illustrates the effect of single agent (SA) dose of a mu anti-PD-L1 mAb in CT26.KRAS12C-Clone #12:B2G9 Syngeneic Colorectal (CRC) Tumors in Balb/c Mice.

The following abbreviations are used herein:

| CAS | Chemical Abstracts Service | IHC | immunohistochemistry |
| --- | --- | --- | --- |
| CDR | complementarity determining region | ORR | overall response rate/ objective response rate |
| CR | complete response | OS | overall survival |
| DNA | deoxyribonucleic acid | PD-1 | programmed death 1 |
| DOR | duration of response | PD-L1 | programmed death ligand 1 |
| Fab | fragment antigen-binding | PD-L2 | programmed death ligand 2 |
| Fc | fragment crystallizable | PFS | progression-free survival |
| FFPE | formalin-fixed and paraffin-embedded | PR | partial response |
| FR | framework | RNA | ribonucleic acid |
| HVR | hypervariable region | SLD | sum of the longest diameters |
| NSCLC | non-small cell lung cancer | NGS | next generation sequencing |

Unless defined otherwise, all technical and scientific terms used herein have the same meaning as commonly understood by those of ordinary skill in the art to which the invention belongs. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention.

The following definitions are provided to facilitate understanding of certain terms used frequently herein and are not meant to limit the scope of the present disclosure. All references referred to herein are incorporated by reference in their entirety.

As used herein, and unless otherwise specified, the terms "about" and "approximately," when referring to doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. The equivalent dose, amount, or weight percent can be within 30%, 20%, 15%, 10%, 5%, 1%, or less of the specified dose, amount, or weight percent.

A "KRas$^{G12C}$ inhibitor" as used herein refers to a covalent inhibitor that specifically binds to a mutant KRas protein comprising a Gly to Cys mutation at a position corresponding to residue 12.

"Compound 1" refers to a compound having structure:

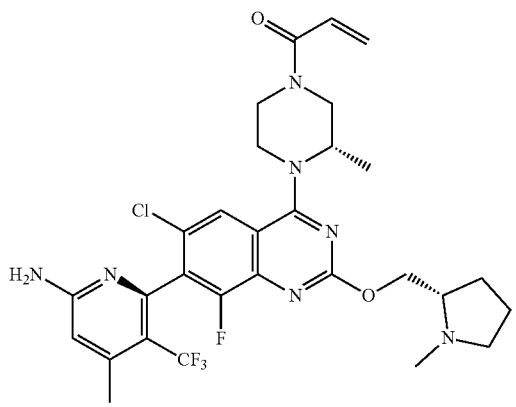

having the chemical name 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one. In one embodiment, Compound 1 is an adipate salt.

The term "pharmaceutically acceptable" refers to molecular entities and compositions that do not produce an adverse, allergic or other untoward reaction when administered to an animal, such as, for example, a human, as appropriate.

Compounds of the invention may be in the form of a salt, such as a pharmaceutically acceptable salt. "Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like. In one embodiment, the salt is formed with adipic acid.

The term "pharmaceutically acceptable base addition salts" include those derived from inorganic bases such as sodium, potassium, lithium, ammonium, calcium, magnesium, iron, zinc, copper, manganese, aluminum salts and the like. Particular base addition salts are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particular organic non-toxic bases include isopropylamine, diethylamine, ethanolamine, tromethamine, dicyclohexylamine, choline, and caffeine.

In some embodiments, a salt is selected from a hydrochloride, hydrobromide, trifluoroacetate, sulfate, phosphate, acetate, fumarate, maleate, tartrate, lactate, citrate, pyruvate, succinate, oxalate, methanesulfonate, p-toluenesulfonate, bisulfate, benzenesulfonate, ethanesulfonate, malonate, xinafoate, ascorbate, oleate, nicotinate, saccharinate, adipate, formate, glycolate, palmitate, L-lactate, D-lactate, aspartate, malate, L-tartrate, D-tartrate, stearate, furoate (e.g., 2-furoate or 3-furoate), napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isothionate (2-hydroxyethylsulfonate), 2-mesitylenesulfonate, 2-naphthalenesulfonate, 2,5-dichlorobenzenesulfonate, D-mandelate, L-mandelate, cinnamate, benzoate, adipate, esylate, malonate, mesitylate (2-mesitylenesulfonate), napsylate (2-naphthalenesulfonate), camsylate (camphor-10-sulfonate, for example (1S)-(+)-10-camphorsulfonic acid salt), glutamate, glutarate, hippurate (2-(benzoylamino)acetate), orotate, xylate (p-xylene-2-sulfonate), and pamoic (2,2'-dihydroxy-1,1'-dinaphthylmethane-3,3'-dicarboxylate).

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity compared to normal.

The terms "PD-L1 binding antagonist", "PD-L1 inhibitor", and "PD-L1 blocking antibody" are used interchangeably herein and refer to a molecule that decreases, blocks, inhibits, abrogates, or interferes with signal transduction resulting from the interaction of PD-L1 with either one or more of its binding partners, such as PD-1 and/or B7-1. In some instances, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some instances, the PD-L1 binding antagonists include anti-PD-L1 antibodies, antigen-binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1 and/or B7-1. In one instance, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some instances, the PD-L1 binding antagonist binds to PD-L1. In some instances, a PD-L1 binding antagonist is an anti-PD-L1 antibody (e.g., an anti-PD-L1 antagonist antibody). Exemplary anti-PD-L1 antagonist antibodies include atezolizumab, MDX-1105, MED14736 (durvalumab), MSB0010718C (avelumab), SHR-1316, CS1001, envafolimab, TQB2450, ZKAB001, LP-002, CX-072, IMC-001, KL-A167, APL-502, cosibelimab, lodapolimab, FAZ053, TG-1501, BGB-A333, BCD-135, AK-106, LDP, GR1405, HLX20, MSB2311, RC98, PDL-GEX, KD036, KY1003, YBL-007, and HS-636. In a preferred aspect, the PD-L1 binding antagonist is atezolizumab.

The terms "programmed death ligand 1" and "PD-L1" refer herein to native sequence human PD-L1 polypeptide. Native sequence PD-L1 polypeptides are provided under Uniprot Accession No. Q9NZQ7. For example, the native sequence PD-L1 may have the amino acid sequence as set forth in Uniprot Accession No. Q9NZQ7-1 (isoform 1). In another example, the native sequence PD-L1 may have the amino acid sequence as set forth in Uniprot Accession No. Q9NZQ7-2 (isoform 2). In yet another example, the native sequence PD-L1 may have the amino acid sequence as set forth in Uniprot Accession No. Q9NZQ7-3 (isoform 3). PD-L1 is also referred to in the art as "programmed cell death 1 ligand 1," "PDCD1LG1," "CD274," "B7-H," and "PDL1."

The Kabat numbering system is generally used when referring to a residue in the variable domain (approximately residues 1-107 of the light chain and residues 1-113 of the heavy chain) (e.g., Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

For the purposes herein, "atezolizumab" is an Fc-engineered, humanized, non-glycosylated IgG1 kappa immunoglobulin that binds PD-L1 and comprises the heavy chain sequence of SEQ ID NO: 1 and the light chain sequence of SEQ ID NO: 2. Atezolizumab comprises a single amino acid substitution (asparagine to alanine) at position 297 on the heavy chain (N297A) using EU numbering of Fc region amino acid residues, which results in a non-glycosylated antibody that has minimal binding to Fc receptors. Atezolizumab is also described in WHO Drug Information (International Nonproprietary Names for Pharmaceutical Substances), Proposed INN: List 112, Vol. 28, No. 4, published Jan. 16, 2015 (see page 485).

In some instances, the anti-PD-L1 antibody comprises (a) a VH comprising an amino acid sequence comprising having at least 95% sequence identity (e.g., at least 95%, 96%, 97%, 98%, or 99% sequence identity) to, or the sequence of SEQ ID NO: 1; (b) a VL comprising an amino acid sequence comprising having at least 95% sequence identity (e.g., at least 95%, 96%, 97%, 98%, or 99% sequence identity) to, or the sequence of SEQ ID NO: 2; or (c) a VH as in (a) and a VL as in (b).

In one embodiment, the anti-PD-L1 antibody comprises atezolizumab, which comprises:

(a) the heavy chain (VH) amino acid sequence:
(SEQ ID NO: 1)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPG,
and

-continued (b) the light chain (VL) amino acid sequence:
(SEQ ID NO: 2)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

The term "cancer" refers to a disease caused by an uncontrolled division of abnormal cells in a part of the body. In one instance, the cancer is lung cancer. In another instance, the cancer is NSCLC. "Cancer" as used herein, refers to cancer characterized as having a $KRas^{G12C}$ mutation.

As used herein, "treating" comprises effective cancer treatment with an effective amount of a therapeutic agent (e.g., atezolizumab or Compound 1 or a pharmaceutically acceptable salt thereof) or combination of therapeutic agents (e.g., atezolizumab and Compound 1 or a pharmaceutically acceptable salt thereof). The treatment may be first-line treatment (e.g., the patient may be previously untreated or not have received prior systemic therapy), or second line or later treatment. For example, a patient is successfully "treated" if one or more symptoms associated with a cancer described herein are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, and/or prolonging survival of patients.

The term "delaying progression" of a disease refers to deferring, hindering, slowing, retarding, stabilizing, and/or postponing development of a cancer described herein. This delay can be of varying lengths of time, depending on the history of the cancer described herein and/or patient being treated. As is evident to one skilled in the art, a sufficient or significant delay can, in effect, encompass prevention, in that the patient does not develop the cancer.

Herein, an "effective amount" refers to the amount of a therapeutic agent described herein (e.g., atezolizumab and/or Compound 1 or a pharmaceutically acceptable salt thereof) that achieves a therapeutic result. In some examples, the effective amount of a therapeutic agent or a combination of therapeutic agents is the amount of the agent or of the combination of agents that achieves a clinical endpoint as provided herein. An effective amount herein may vary according to factors such as the disease state, age, sex, and weight of the patient, and the ability of the agent to elicit a desired response in the patient. An effective amount is also one in which any toxic or detrimental effects of the treatment are outweighed by the therapeutically beneficial effects. In some embodiments, an effective amount of the drug may have the effect in reducing the number of cancer cells; reducing the tumor size; inhibiting (i.e., slow or stop) cancer cell infiltration into peripheral organs; inhibit (i.e., slow or stop) tumor metastasis; inhibiting (i.e., slow or stop) tumor growth; and/or relieving one or more of the symptoms associated with the disease. An effective amount can be administered in one or more administrations. An effective amount of drug, compound, pharmaceutical composition, or combination therapy described herein can be an amount sufficient to accomplish therapeutic treatment either directly or indirectly.

"Objective response rate" or "ORR" refers the percentage of patients with a confirmed complete response or partial response on two consecutive occasions 4 weeks apart, as determined by the investigator according to RECIST v1.1.

"Duration of response" or "DOR" refers to the time from the first occurrence of a documented objective response to disease progression, as determined by the investigator according to RECIST v1.1, or death from any cause, whichever occurs first.

"Progression free survival" or "PFS" refers to the time from enrollment to the date of the first recorded occurrence of disease progression, as determined by the investigator using RECIST v1.1 or death from any cause, whichever occurs first.

As used herein, "complete response" and "CR" refers to disappearance of all target lesions and (if applicable) normalization of tumor marker level.

As used herein, "partial response" and "PR" refers to persistence of one or more non-target lesions and/or (if applicable) maintenance of tumor marker level above the normal limits. A PR can also refer to 30% decrease in sum of diameters of target lesions, in the absence of CR, new lesions, and unequivocal progression in non-target lesions.

An "administration period" or "cycle" refers to a period of time comprising administration of one or more agents described herein (e.g. Compound 1 or a pharmaceutically acceptable salt thereof and atezolizumab) and an optional period of time comprising no administration of one or more of the agents described herein. For example, a cycle can be 21 days in total and include administration of one or more agents described herein (e.g. Compound 1 or a pharmaceutically acceptable salt thereof and atezolizumab) each day of the cycle. In another example, a cycle can be 28 days in total length and include administration of one or more agents described herein (e.g. Compound 1 or a pharmaceutically acceptable salt thereof and atezolizumab) for 21 days and a rest period of 7 days. A "rest period" refers to a period of time where at least one of the agents described herein (i.e. Compound 1 or a pharmaceutically acceptable salt thereof and atezolizumab) are not administered. In one embodiment, a rest period refers to a period of time where none of the agents described herein (i.e. Compound 1 or a pharmaceutically acceptable salt thereof and atezolizumab) are administered. A rest period as provided herein can in some instances include administration of another agent that is not Compound 1 or a pharmaceutically acceptable salt thereof or atezolizumab. In such instances, administration of another agent during a rest period should not interfere or detriment administration of an agent described herein. In one instance, cycle as used herein refers to 21 day cycles without a rest period.

A "dosing regimen" refers to a period of administration of the agents described herein comprising one or more cycles, where each cycle can include administration of the agents described herein at different times or in different amounts.

"QD" refers to administration of an agent described herein once daily.

"BID" refers to administration of an agent described herein twice daily.

"Q3W" refers to administration of an agent described herein once every three weeks.

"PO" refers to oral administration of an agent described herein.

"IV" refers to intravenous administration of any agent described herein.

A graded adverse event refers to the severity grading scale as established for by NCI CTCAE. In one embodiment, the adverse event is graded in accordance with the table below.

| Grade | Severity |
|---|---|
| 1 | Mild; asymptomatic or mild symptoms; clinical or diagnostic observations only; or intervention not indicated |
| 2 | Moderate; minimal, local, or non-invasive intervention indicated; or limiting age-appropriate instrumental activities of daily living[a] |
| 3 | Severe or medically significant, but not immediately life-threatening; hospitalization or prolongation of hospitalization indicated; disabling; or limiting self-care activities of daily living[b,c] |
| 4 | Life-threatening consequences or urgent intervention indicated[d] |
| 5 | Death related to adverse event[d] |

The term "patient" refers to a human patient. A patient may be an adult.

The term "antibody" herein specifically covers monoclonal antibodies (including full-length monoclonal antibodies), polyclonal antibodies, multispecific antibodies (e.g., bispecific antibodies), and antibody fragments so long as they exhibit the desired biological activity. In one instance, the antibody is a full-length monoclonal antibody.

The term IgG "isotype" or "subclass" as used herein is meant any of the subclasses of immunoglobulins defined by the chemical and antigenic characteristics of their constant regions.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, γ, ε, γ, and μ, respectively. The subunit structures and three-dimensional configurations of different classes of immunoglobulins are well known and described generally in, for example, Abbas et al. Cellular and Mol. Immunology, 4th ed. (W.B. Saunders, Co., 2000). An antibody may be part of a larger fusion molecule, formed by covalent or non-covalent association of the antibody with one or more other proteins or peptides.

The terms "full-length antibody," "intact antibody," and "whole antibody" are used herein interchangeably to refer to an antibody in its substantially intact form, not antibody fragments as defined below. The terms refer to an antibody comprising an Fc region.

The term "Fc region" herein is used to define a C-terminal region of an immunoglobulin heavy chain that contains at least a portion of the constant region. The term includes native sequence Fc regions and variant Fc regions. In one aspect, a human IgG heavy chain Fc region extends from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore, an antibody produced by a host cell by expression of a specific nucleic acid molecule encoding a full-length heavy chain may include the full-length heavy chain, or it may include a cleaved variant of the full-length heavy chain. This may be the case where the final two C-terminal amino acids of the heavy chain are glycine (G446) and lysine (K447). Therefore, the C-terminal lysine (Lys447), or the C-terminal glycine (Gly446) and lysine (Lys447), of the Fc region may or may not be present. Amino acid sequences of heavy chains including an Fc region are denoted herein without the C-terminal lysine (Lys447) if not indicated otherwise. In one aspect, a heavy chain including an Fc region as specified herein, comprised in an antibody disclosed herein, comprises an additional C-terminal glycine-lysine dipeptide (G446 and K447). In one aspect, a heavy chain including an Fc region as specified herein, comprised in an antibody disclosed herein, comprises an additional C-terminal glycine residue (G446). In one aspect, a heavy chain including an Fc region as specified herein, comprised in an antibody disclosed herein, comprises an additional C-terminal lysine residue (K447). In one embodiment, the Fc region contains a single amino acid substitution N297A of the heavy chain. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, MD, 1991.

A "naked antibody" refers to an antibody that is not conjugated to a heterologous moiety (e.g., a cytotoxic moiety) or radiolabel. The naked antibody may be present in a pharmaceutical composition.

"Antibody fragments" comprise a portion of an intact antibody, preferably comprising the antigen-binding region thereof. In some instances, the antibody fragment described herein is an antigen-binding fragment. Examples of antibody fragments include Fab, Fab', F(ab')$_2$, and Fv fragments; diabodies; linear antibodies; single-chain antibody molecules (e.g., scFvs); and multispecific antibodies formed from antibody fragments.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies in accordance with the present invention may be made by a variety of techniques, including but not limited to the hybridoma method, recombinant DNA methods, phage-display methods, and methods utilizing transgenic animals containing all or part of the human immunoglobulin loci.

The term "hypervariable region" or "HVR" as used herein refers to each of the regions of an antibody variable domain which are hypervariable in sequence and which determine antigen binding specificity, for example "complementarity determining regions" ("CDRs").

Generally, antibodies comprise six CDRs: three in the VH (CDR-H1, CDR-H2, CDR-H3), and three in the VL (CDR-L1, CDR-L2, CDR-L3). Exemplary CDRs herein include:
(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, MD (1991)); and (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)).

Unless otherwise indicated, the CDRs are determined according to Kabat et al., supra. One of skill in the art will understand that the CDR designations can also be determined according to Chothia, supra, McCallum, supra, or any other scientifically accepted nomenclature system.

"Framework" or "FR" refers to variable domain residues other than complementary determining regions (CDRs). The FR of a variable domain generally consists of four FR domains: FR1, FR2, FR3, and FR4. Accordingly, the CDR and FR sequences generally appear in the following sequence in VH (or VL): FR1-CDR-H1(CDR-L1)-FR2-CDR-H2(CDR-L2)-FR3-CDR-H3(CDR-L3)-FR4.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g., residues 82a, 82b, and 82c, etc., according to Kabat) after heavy chain FR residue 82. The Kabat numbering of residues may be determined for a given antibody by alignment at regions of homology of the sequence of the antibody with a "standard" Kabat numbered sequence.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "in combination with" refers to administration of one treatment modality in addition to another treatment modality, for example, a treatment regimen that includes administration of a PD-1 axis binding antagonist (e.g., atezolizumab) and Compound 1 or a pharmaceutically acceptable salt thereof. As such, "in combination with" refers to administration of one treatment modality before, during, or after administration of the other treatment modality to the patient.

A drug that is administered "concurrently" with one or more other drugs is administered during the same treatment cycle, on the same day of treatment, as the one or more other drugs, and, optionally, at the same time as the one or more other drugs. For instance, for cancer therapies given every 3 weeks, the concurrently administered drugs are each administered on day 1 of a 3 week cycle.

Combination Therapies

Provided herein are combination therapies (compositions) comprising Compound 1 or a pharmaceutically acceptable salt thereof (e.g. Compound 1 adipate) and a PD-L1 binding antagonist.

In some instances, the PD-L1 binding antagonist is an anti-PD-L1 antibody. A variety of anti-PD-L1 antibodies are contemplated and described herein. In any of the instances herein, the isolated anti-PD-L1 antibody can bind to a human PD-L1, for example a human PD-L1 as shown in UniProtKB/Swiss-Prot Accession No. Q9NZQ7-1, or a variant thereof. In some instances, the anti-PD-L1 antibody is capable of inhibiting binding between PD-L1 and PD-1 and/or between PD-L1 and B7-1. In some instances, the anti-PD-L1 antibody is a monoclonal antibody. In some instances, the anti-PD-L1 antibody is an antibody fragment selected from the group consisting of Fab, Fab'-SH, Fv, scFv, and (Fab')2 fragments. In some instances, the anti-PD-L1 antibody is a humanized antibody. In some instances, the anti-PD-L1 antibody is a human antibody. Exemplary anti-PD-L1 antibodies include atezolizumab, MDX-1105, MED14736 (durvalumab), MSB0010718C (avelumab), SHR-1316, CS1001, envafolimab, TQB2450, ZKAB001, LP-002, CX-072, IMC-001, KL-A167, APL-502, cosibelimab, lodapolimab, FAZ053, TG-1501, BGB-A333, BCD-135, AK-106, LDP, GR1405, HLX20, MSB2311, RC98, PDL-GEX, KD036, KY1003, YBL-007, and HS-636. Examples of anti-PD-L1 antibodies useful in the methods of this invention and methods of making them are described in International Patent Application Publication No. WO 2010/077634 and U.S. Pat. No. 8,217,149, each of which is incorporated herein by reference in its entirety.

In some instances, the anti-PD-L1 antibody comprises:

```
(a) an HVR-H1, HVR-H2, and HVR-H3 sequence of
                                        (SEQ ID NO: 3)
GFTFSDSWIH, (SEQ ID NO: 4)
AWISPYGGSTYYADSVKG
and (SEQ ID NO: 5)
RHWPGGFDY,
respectively, and (b) an HVR-L1, HVR-L2, and HVR-L3 sequence of
                                        (SEQ ID NO: 6)
RASQDVSTAVA, (SEQ ID NO: 7)
SASFLYS
and
                                        (SEQ ID NO: 8)
QQYLYHPAT,
respectively.
```

In one embodiment, the anti-PD-L1 antibody comprises:

```
(a) a heavy chain variable region (VH) comprising
the amino acid sequence:
                                        (SEQ ID NO: 9)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSS,
and (b) the light chain variable region (VL)
comprising the amino acid sequence:
                                        (SEQ ID NO: 10)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.
```

In some instances, the anti-PD-L1 antibody comprises (a) a VH comprising an amino acid sequence comprising having at least 95% sequence identity (e.g., at least 95%, 96%, 97%, 98%, or 99% sequence identity) to, or the sequence of SEQ ID NO: 9; (b) a VL comprising an amino acid sequence comprising having at least 95% sequence identity (e.g., at least 95%, 96%, 97%, 98%, or 99% sequence identity) to, or the sequence of SEQ ID NO: 10; or (c) a VH as in (a) and a VL as in (b).

In one embodiment, the anti-PD-L1 antibody comprises atezolizumab, which comprises:

```
(a) the heavy chain amino acid sequence:
                                     (SEQ ID NO: 1)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPG,
and (b) the light chain amino acid sequence:
                                     (SEQ ID NO: 2)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.
```

In some instances, the anti-PD-L1 antibody is avelumab (CAS Registry Number: 1537032-82-8). Avelumab, also known as MSB0010718C, is a human monoclonal IgG1 anti-PD-L1 antibody (Merck KGaA, Pfizer).

In some instances, the anti-PD-L1 antibody is durvalumab (CAS Registry Number: 1428935-60-7). Durvalumab, also known as MED14736, is an Fc-optimized human monoclonal IgG1 kappa anti-PD-L1 antibody (MedImmune, AstraZeneca) described in WO 2011/066389 and US 2013/034559.

In some instances, the anti-PD-L1 antibody is MDX-1105 (Bristol Myers Squibb). MDX-1105, also known as BMS-936559, is an anti-PD-L1 antibody described in WO 2007/005874.

In some instances, the anti-PD-L1 antibody is LY3300054 (Eli Lilly).

In some instances, the anti-PD-L1 antibody is STI-A1014 (Sorrento). STI-A1014 is a human anti-PD-L1 antibody.

In some instances, the anti-PD-L1 antibody is KN035 (Suzhou Alphamab). KN035 is single-domain antibody (dAB) generated from a camel phage display library.

In some instances, the anti-PD-L1 antibody comprises a cleavable moiety or linker that, when cleaved (e.g., by a protease in the tumor microenvironment), activates an antibody antigen binding domain to allow it to bind its antigen, e.g., by removing a non-binding steric moiety. In some instances, the anti-PD-L1 antibody is CX-072 (CytomX Therapeutics).

In some instances, the anti-PD-L1 antibody comprises the six HVR sequences (e.g., the three heavy chain HVRs and the three light chain HVRs) and/or the heavy chain variable domain and light chain variable domain from an anti-PD-L1 antibody described in US 20160108123, WO 2016/000619, WO 2012/145493, U.S. Pat. No. 9,205,148, WO 2013/181634, or WO 2016/061142.

In a still further specific aspect, the anti-PD-L1 antibody has reduced or minimal effector function. In a still further specific aspect, the minimal effector function results from an "effector-less Fc mutation" or a glycosylation mutation. In still a further instance, the effector-less Fc mutation is an N297A or D265A/N297A substitution in the constant region. In still a further instance, the effector-less Fc mutation is an N297A substitution in the constant region. In some instances, the isolated anti-PD-L1 antibody is aglycosylated. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. Removal of glycosylation sites from an antibody is conveniently accomplished by altering the amino acid sequence such that one of the above-described tripeptide sequences (for N-linked glycosylation sites) is removed. The alteration may be made by substitution of an asparagine, serine or threonine residue within the glycosylation site with another amino acid residue (e.g., glycine, alanine, or a conservative substitution).

In one aspect provided herein is a combination therapy comprising Compound 1 or a pharmaceutically acceptable salt thereof (e.g. Compound 1 adipate) and atezolizumab. In one embodiment, the combination therapies described herein are useful in the treatment of certain types of lung cancer as described herein.

In one aspect provided herein is a combination therapy comprising Compound 1 or a pharmaceutically acceptable salt thereof administered QD on days 1-21 of a first 21-day cycle and an anti-PD-L1 antibody.

In one aspect provided herein is a combination therapy comprising Compound 1 or a pharmaceutically acceptable salt thereof administered QD on days 1-21 of a first 21-day cycle and atezolizumab administered Q3W on day 1 of the first 21-day cycle.

In one embodiment of the combination therapies described herein, Compound 1 or a pharmaceutically acceptable salt thereof is administered as a fixed dose QD administration. In one embodiment, the administration is oral (PO), where Compound 1 or a pharmaceutically acceptable salt thereof is formulated as a tablet or capsule. In one such embodiment, Compound 1 or a pharmaceutically acceptable salt thereof is formulated (and administered) as a film coated tablet.

In one embodiment of the combination therapies described herein, Compound 1 or a pharmaceutically acceptable salt thereof is administered at an amount of about 5 mg-600 mg, 5 mg-500 mg, 5 mg-400 mg, 5 mg-300 mg, 5 mg-250 mg, 5 mg-200 mg, 5 mg-150 mg, 5 mg-100 mg, 5 mg-50 mg, 5 mg-25 mg, 25 mg-600 mg, 25 mg-500 mg, 25 mg-400 mg, 25 mg-300 mg, 25 mg-250 mg, 25 mg-200 mg, 25 mg-150 mg, 25 mg-100 mg, 25 mg-50 mg, 50 mg-600 mg, 50 mg-500 mg, 50 mg-400 mg, 50 mg-300 mg, 50 mg-250 mg, 50 mg-200 mg, 50 mg-150 mg, or 50 mg-100 mg QD. In another embodiment, Compound 1 or a pharmaceutically acceptable salt thereof is administered at an amount of about 5 mg, 25 mg, 50 mg, 100 mg, 150 mg, 200 mg, 250 mg, 300 mg, 400 mg or 500 mg. In another embodiment, Compound 1 or a pharmaceutically acceptable salt thereof is administered at an amount of about 50 mg, 100 mg, 200 mg, 300 mg, or 400 mg. In another embodiment, Compound 1 or a pharmaceutically acceptable salt thereof is administered at an amount of about 50 mg, 100 mg, 200 mg, or 400 mg. In one preferred embodiment, Compound 1 or a pharmaceutically acceptable salt thereof of the combination therapies described herein is administered as an adipate salt. In such embodiments, the amount of Compound 1 or a pharmaceutically acceptable salt thereof is administered as an amount relative to the free-base form. In one embodiment, Compound 1 or a pharmaceutically acceptable salt thereof is administered BID in an amount as described herein (e.g. 50 mg, 100 mg, 200 mg, or 400 mg).

In one embodiment of the combination therapy described herein, the PD-L1 binding antagonist is administered in accordance with a package insert. In a preferred embodiment, the PD-L1 binding antagonist is atezolizumab.

As a general proposition, the therapeutically effective amount of a PD-L1 binding antagonist (e.g., atezolizumab) administered to a human will be in the range of about 0.01 to about 50 mg/kg of patient body weight, whether by one or more administrations.

In some exemplary embodiments, the PD-L1 binding antagonist is administered in a dose of about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, weekly, every two weeks, every three weeks, or every four weeks, for example.

In one instance, a PD-L1 binding antagonist is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, or about 1500 mg. In some instances, the PD-L1 binding antagonist may be administered at a dose of about 1000 mg to about 1400 mg every three weeks (e.g., about 1100 mg to about 1300 mg every three weeks, e.g., about 1150 mg to about 1250 mg every three weeks).

In one preferred embodiment, the combination therapies described herein comprise Compound 1 or a pharmaceutically acceptable salt thereof as described herein and atezolizumab, where atezolizumab is administered to the patient intravenously at a dose of about 840 mg every 2 weeks (Q2W), about 1200 mg every 3 weeks (Q3W), or about 1680 mg of every 4 weeks (Q4W). In one preferred embodiment, the combination therapies described herein comprise Compound 1 or a pharmaceutically acceptable salt thereof as described herein and atezolizumab, where atezolizumab is administered to the patient intravenously at a dose of about 1200 mg Q3W. In one such embodiment, the combination therapies described herein comprise Compound 1 or a pharmaceutically acceptable salt thereof as described herein administered at a dose of about 50 mg, 100 mg, 200 mg, or 400 mg PO QD, and atezolizumab, where atezolizumab is administered to the patient intravenously at a dose of about 1200 mg Q3W.

In one embodiment, the combination therapies described herein are used for treating lung cancer comprising a $KRas^{G12C}$ mutation. In one particular embodiment, the combination therapy comprises Compound 1 or a pharmaceutically acceptable salt thereof (e.g. Compound 1 adipate) and atezolizumab, where the combination therapy is for treating lung cancer comprising a $KRas^{G12C}$ mutation as described herein. In one such embodiment, the lung cancer is non-small cell lung carcinoma (NSCLC). In another such embodiment, the lung cancer is adenocarcinoma, squamous-cell lung carcinoma or large-cell lung carcinoma. The lung cancer can be stage I or II lung cancer. In one embodiment, the lung cancer is stage III or IV lung cancer.

In another aspect provided herein is a combination therapy useful in the treatment of lung cancer comprising a $KRas^{G12C}$ mutation where the combination therapy comprises Compound 1 or a pharmaceutically acceptable salt thereof (e.g. Compound 1 adipate) and atezolizumab. In one such embodiment, the lung cancer is NSCLC.

In still another aspect provided herein is a combination therapy useful in the treatment of lung cancer comprising a $KRas^{G12C}$ mutation where the combination therapy comprises Compound 1 or a pharmaceutically acceptable salt thereof (e.g. Compound 1 adipate) where Compound 1 or a pharmaceutically acceptable salt thereof is administered QD on days 1-21 of a first 21-day cycle and atezolizumab is administered Q3W on day 1 of the first 21-day cycle. In one preferred embodiment, the lung cancer is NSCLC.

In still another aspect provided herein is a combination therapy useful in the treatment of lung cancer comprising a $KRas^{G12C}$ mutation where the combination therapy comprises Compound 1 or a pharmaceutically acceptable salt thereof (e.g. Compound 1 adipate) where Compound 1 or a pharmaceutically acceptable salt thereof is administered QD at an amount of about 50 mg-400 mg on days 1-21 of a first 21-day cycle and atezolizumab is administered Q3W at an amount of about 1200 mg on day 1 of the first 21-day cycle. In one preferred embodiment, the lung cancer is NSCLC.

Methods of Treating

Also provided herein are methods of treating lung cancer mediated by a $KRas^{G12C}$ mutation in a patient having lung cancer. In one aspect provided herein is a method of treating lung cancer mediated by a $KRas^{G12C}$ mutation in a patient having such a lung cancer, the method comprising administering an effective amount of a combination therapy comprising Compound 1 or a pharmaceutically acceptable salt thereof (e.g. Compound 1 adipate) and a PD-L1 binding antagonist. In one aspect provided herein is a method of treating lung cancer mediated by a $KRas^{G12C}$ mutation in a patient having such a lung cancer, the method comprising administering an effective amount of a combination therapy comprising Compound 1 or a pharmaceutically acceptable salt thereof (e.g. Compound 1 adipate) and atezolizumab. In one embodiment, the methods further include a rest period of 7 days.

In one embodiment of the methods provided herein, the lung cancer is non-small cell lung carcinoma (NSCLC). In another embodiment of the methods provided herein, the lung cancer is adenocarcinoma, squamous-cell lung carcinoma or large-cell lung carcinoma. In one such embodiment, the cancer is lung adenocarcinoma. In another such embodiment, the lung cancer is a small cell lung carcinoma. In another embodiment, the lung cancer is small cell lung carcinoma. In still another embodiment, the lung cancer is glandular tumors, carcinoid tumors or undifferentiated carcinomas. The lung cancer can be stage I or II lung cancer. In one embodiment, the lung cancer is stage III or IV lung cancer.

Also provided herein is a method of treating NSCLC comprising a KRas$^{G12C}$ mutation in a patient having such a cancer, where the method comprises administering to the patient a combination therapy as described herein comprising a dosing regimen comprising: (i) administering Compound 1 or a pharmaceutically acceptable salt thereof QD on days 1-21 of a first 21-day cycle; and (ii) administering atezolizumab Q3W on day 1 of the first 21-day cycle. In one embodiment of the method provided herein, the method is used for treating adenocarcinoma. In one embodiment of the method provided herein, the method comprises 2 or more cycles. In one such embodiment, the methods further include a rest period of 7 days between cycles.

In one embodiment of the methods described herein, Compound 1 or a pharmaceutically acceptable salt thereof is administered as a fixed dose QD administration. In one embodiment, the administration is oral (PO), where Compound 1 or a pharmaceutically acceptable salt thereof is formulated as a tablet or capsule. In one embodiment, Compound 1 or a pharmaceutically acceptable salt thereof is administered at an amount of 5 mg-600 mg, 5 mg-500 mg, 5 mg-400 mg, 5 mg-300 mg, 5 mg-250 mg, 5 mg-200 mg, 5 mg-150 mg, 5 mg-100 mg, 5 mg-50 mg, 5 mg-25 mg, 25 mg-600 mg, 25 mg-500 mg, 25 mg-400 mg, 25 mg-300 mg, 25 mg-250 mg, 25 mg-200 mg, 25 mg-150 mg, 25 mg-100 mg, 25 mg-50 mg, 50 mg-600 mg, 50 mg-500 mg, 50 mg-400 mg, 50 mg-300 mg, 50 mg-250 mg, 50 mg-200 mg, 50 mg-150 mg, or 50 mg-100 mg QD. In another embodiment, Compound 1 or a pharmaceutically acceptable salt thereof is administered at an amount of about 5 mg, 25 mg, 50 mg, 100 mg, 150 mg, 200 mg, 250 mg, 300 mg, 400 mg or 500 mg. In another embodiment, Compound 1 or a pharmaceutically acceptable salt thereof is administered at an amount of about 50 mg, 100 mg, 200 mg, 300 mg, or 400 mg. In another embodiment, Compound 1 or a pharmaceutically acceptable salt thereof is administered at an amount of about 50 mg, 100 mg, 200 mg, or 400 mg. In one preferred embodiment, Compound 1 of the combination therapies described herein is administered as an adipate salt. In such embodiments, the amount of Compound 1 or a pharmaceutically acceptable salt thereof is administered as an amount relative to the free-base form.

In one embodiment of the methods described herein, atezolizumab is administered in a dose of about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, weekly, every two weeks, every three weeks, or every four weeks, for example.

In one instance, atezolizumab is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, or about 1500 mg. In some instances, atezolizumab may be administered at a dose of about 1000 mg to about 1400 mg every three weeks (e.g., about 1100 mg to about 1300 mg every three weeks, e.g., about 1150 mg to about 1250 mg every three weeks).

In one preferred embodiment of the methods described herein, Compound 1 or a pharmaceutically acceptable salt thereof is administered as described herein and atezolizumab is administered to the patient intravenously at a dose of about 1200 mg Q3W.

Also provided herein is a method of treating NSCLC comprising a KRas$^{G12C}$ mutation in a patient having such a cancer, where the method comprises administering to the patient a combination therapy as described herein comprising a dosing regimen comprising: (i) administering Compound 1 or a pharmaceutically acceptable salt thereof at an amount of about 50 mg-500 mg QD on days 1-21 of a first 21-day cycle; and (ii) administering atezolizumab Q3W at an amount of 1200 mg on day 1 of the first 21-day cycle. In one embodiment of the method provided herein, the method is used for treating adenocarcinoma.

The methods provided herein can include administration of a combination therapy described herein as part of a dosing regimen. In such one embodiment, the dosing regimen comprises one or more cycles. In another embodiment, the dosing regimen comprises at least 2 cycles. In another aspect provided herein is the dosing regimen comprises 2, 3, 4, 5, 6, 8, 10, 12, 16, 18, 20, 24, 30, 36, 42, 48, 54, 60, 66, or 72 cycles. In still another embodiment, dosing regimen comprises about 2-72, 2-66, 2-60, 2-54, 2-48, 2-42, 2-36, 2-30, 2-24, 2-18, 2-12, or 2-6 cycles. In one embodiment, the dosing regimen includes administration of a combination therapy as described herein in any number of cycles until the desired response (e.g. PFS, OS, ORR, and/or DOR) reaches a desired outcome (e.g. increase in PFS, OS, ORR, and/or DOR compared to a control described herein). In another embodiment, the dosing regimen includes administration of a combination therapy as described herein in any number of cycles until toxicity develops or the patient otherwise experiences one or more adverse events (AEs) that prevents further administration. In still another embodiment, the dosing regimen includes administration of a combination therapy as described herein in any number of cycles until disease progression.

In one embodiment of the methods described herein, a patient is administered a total of 1 to 50 doses of atezolizumab, e.g., 1 to 50 doses, 1 to 45 doses, 1 to 40 doses, 1 to 35 doses, 1 to 30 doses, 1 to 25 doses, 1 to 20 doses, 1 to 15 doses, 1 to 10 doses, 1 to 5 doses, 2 to 50 doses, 2 to 45 doses, 2 to 40 doses, 2 to 35 doses, 2 to 30 doses, 2 to 25 doses, 2 to 20 doses, 2 to 15 doses, 2 to 10 doses, 2 to 5 doses, 3 to 50 doses, 3 to 45 doses, 3 to 40 doses, 3 to 35 doses, 3 to 30 doses, 3 to 25 doses, 3 to 20 doses, 3 to 15 doses, 3 to 10 doses, 3 to 5 doses, 4 to 50 doses, 4 to 45 doses, 4 to 40 doses, 4 to 35 doses, 4 to 30 doses, 4 to 25 doses, 4 to 20 doses, 4 to 15 doses, 4 to 10 doses, 4 to 5 doses, 5 to 50 doses, 5 to 45 doses, 5 to 40 doses, 5 to 35 doses, 5 to 30 doses, 5 to 25 doses, 5 to 20 doses, 5 to 15 doses, 5 to 10 doses, 10 to 50 doses, 10 to 45 doses, 10 to 40 doses, 10 to 35 doses, 10 to 30 doses, 10 to 25 doses, 10 to 20 doses, 10 to 15 doses, 15 to 50 doses, 15 to 45 doses, 15 to 40 doses, 15 to 35 doses, 15 to 30 doses, 15 to 25 doses, 15 to 20 doses, 20 to 50 doses, 20 to 45 doses, 20 to 40 doses, 20 to 35 doses, 20 to 30 doses, 20 to 25 doses, 25 to 50 doses, 25 to 45 doses, 25 to 40 doses, 25 to 35 doses, 25 to 30 doses, 30 to 50 doses, 30 to 45 doses, 30 to 40 doses, 30 to 35 doses, 35 to 50 doses, 35 to 45 doses, 35 to 40 doses, 40 to 50 doses, 40 to 45 doses, or 45 to 50 doses. In one preferred embodiment, the doses are administered intravenously.

In certain embodiments, the therapeutic agents of the combination therapies described herein (e.g. Compound 1 or a pharmaceutically acceptable salt thereof and atezolizumab) may be administered in any suitable manner known in the art. For example, atezolizumab may be administered sequentially (on different days) or concurrently (on the same day or during the same treatment cycle) as Compound 1 or a pharmaceutically acceptable salt thereof. In one embodiment, atezolizumab is administered after administration of Compound 1 or a pharmaceutically acceptable salt thereof. In some instances, atezolizumab is administered after administration of Compound 1 or a pharmaceutically acceptable salt thereof may be administered on the same day. In one embodiment, atezolizumab may be administered after administration of Compound 1 or a pharmaceutically acceptable salt thereof on the same day. For example, Compound 1 or a pharmaceutically acceptable salt thereof can be administered on Day 1 of each cycle prior to administration of atezolizumab on Day 1 of each cycle, where Compound 1 or a pharmaceutically acceptable salt thereof is then administered QD for the next 20 days of the 21-day cycle.

In a preferred embodiment, atezolizumab is administered intravenously. In one example, atezolizumab may be administered intravenously over 60 minutes; if the first infusion is tolerated, all subsequent infusions may be delivered over 30 minutes. In some examples, the PD-1 axis binding antagonist is not administered as an intravenous push or bolus.

In one embodiment, atezolizumab is administered in accordance with Table 1.

ity of side effects of treatment, such as anti-nausea agents, a corticosteroid (e.g., prednisone or an equivalent, e.g., at a dose of 1-2 mg/kg/day), hormone replacement medicine(s), and the like).

A patient as provided herein, must be evaluated and have a confirmed test result for a KRas$^{G12C}$ mutation as set forth herein. A patient described herein having diagnosed NSCLC must not have a known concomitant second oncogenic driver (e.g., for NSCLC: sensitizing EGFR mutations, ALK rearrangement, ROS1 rearrangement, BRAF V600E mutation, NTRK fusions, RET fusions; or for adenocarcinoma of the colon or rectum: BRAF V600E mutation, ERBB2 amplification). In one embodiment, such second oncogenic drivers are determined using NGS (e.g. by the Foundation Medicine, Inc. (FMI) NGS assay).

In one embodiment, a patient described herein does not have known and untreated, or active central nervous system (CNS) metastases (progressing or requiring anticonvulsants or corticosteroids for symptomatic control). A patient may be treated using the methods described herein where such patients have a history of treated CNS metastases where such a patient has: (1) measurable or evaluable disease outside the CNS; (2) no history of intracranial hemorrhage or spinal cord hemorrhage; (3) no ongoing requirement for

TABLE 1

| First Infusion | Subsequent Infusions |
| --- | --- |
| No premedication is permitted prior to the atezolizunnab infusion.<br>Vital signs (pulse rate, respiratory rate, blood pressure, and temperature) should be measured within 60 minutes prior to the infusion.<br>Atezolizunnab should be infused over 60 (±15) minutes.<br>If clinically indicated, vital signs should be measured every 15 (±5) minutes during the infusion and at 30 (±10) minutes after the infusion.<br>Patients should be informed about the possibility of delayed post-infusion symptoms and instructed to contact their study physician if they develop such symptoms. | If the patient experienced an infusion-related reaction with any previous infusion, premedication with antihistamines, antipyretics, and/or analgesics may be administered for subsequent doses at the discretion of the investigator.<br>Vital signs should be measured within 60 minutes prior to the infusion.<br>Atezolizunnab should be infused over 30 (±10) minutes if the previous infusion was tolerated without an infusion-related reaction, or 60 (±15) minutes if the patient experienced an infusion-related reaction with the previous infusion.<br>If the patient experienced an infusion-related reaction with the previous infusion or if clinically indicated, vital signs should be measured during the infusion and at 30 (±10) minutes after the infusion. |

Also provided herein are methods for treating lung cancer in a patient having such a cancer, where the method comprises administering to the patient a treatment regimen comprising an effective amount of Compound 1 or a pharmaceutically acceptable salt thereof (e.g. adipate salt) and a PD-L1 binding antagonist (e.g., atezolizumab). In one embodiment of such methods, Compound 1 is an adipate salt and the PD-L1 binding antagonist is atezolizumab. In another embodiment of such methods, Compound 1 or a pharmaceutically acceptable salt thereof is administered QD as described herein and in an amount as described herein (e.g. 50 mg-500 mg). In another embodiment of such methods, atezolizumab is administered Q3W as described herein and in an amount as described herein (e.g. 1200 mg). In such methods, Compound 1 or a pharmaceutically acceptable salt thereof and atezolizumab can be administered as described herein.

In some instances, the treatment regimen includes administration of one or more additional therapies where the additional therapy is one or more side-effect limiting agents (e.g., agents intended to lessen the occurrence and/or severcorticosteroids as therapy for CNS metastases, with corticosteroids discontinued for 2 weeks prior to administration of a combination therapy as described herein and no ongoing symptoms attributed to CNS metastases; (4) no stereotactic radiation within 7 days or whole-brain radiation within 14 days prior to Day 1 of Cycle 1 as described herein; and (5) no evidence of interim progression between the completion of CNS-directed therapy and the screening radiographic study.

In one embodiment, a patient described herein has not received prior treatment with a KRas$^{G12C}$ specific inhibitor.

In another embodiment, a patient described herein has not received treatment with chemotherapy, immunotherapy, or biologic therapy as anti-cancer therapy within 3 weeks prior to administration of a combination therapy described herein, or endocrine therapy within 2 weeks prior to administration of a combination therapy described herein, except for the following:

(a) hormonal therapy with gonadotropin-releasing hormone (GnRH) agonists or antagonists for endocrine sensitive cancers (e.g., prostate, endometrial, hormone receptor-positive breast cancer);

(b) kinase inhibitors, approved by regulatory authorities, may be used up to 2 weeks prior to administration of a combination therapy described herein, provided any drug-related toxicity has completely resolved; or (c) treatment with an investigational agent within 3 weeks or five half-lives prior to administration of a combination therapy described herein, whichever is shorter.

In another embodiment, a patient described herein has not received radiation therapy (other than palliative radiation to bony metastases and radiation to CNS metastases as described above) as cancer therapy within 4 weeks prior to initiation of administration of a combination therapy described herein. In still another embodiment, a patient described herein has not received palliative radiation to bony metastases within 2 weeks prior to administration of a combination therapy described herein.

In another embodiment, a patient described herein does not have active or a history of autoimmune disease or immune deficiency, including, but not limited to, myasthenia gravis, myositis, autoimmune hepatitis, myocarditis, systemic lupus erythematosus, rheumatoid arthritis, inflammatory bowel disease, antiphospholipid antibody syndrome, Wegener granulomatosis, Sjögren syndrome, Guillain-Barré syndrome, or multiple sclerosis, with the following exceptions:

(a) Patients with a history of autoimmune-related hypothyroidism who are on thyroid-replacement hormone;

(b) Patients with controlled Type 1 diabetes mellitus who are on an insulin regimen;

(c) Patients with eczema, psoriasis, lichen simplex chronicus, or vitiligo with dermatologic manifestations only (e.g., patients with psoriatic arthritis are excluded) are eligible for treatment with atezolizumab provided all of following conditions are met:

(i) Rash must cover <10% of body surface area (ii) Disease is well controlled on Day 1 and requires only low-potency topical corticosteroids (iii) No occurrence of acute exacerbations of the underlying condition requiring psoralen plus ultraviolet A radiation, methotrexate, retinoids, biologic agents, oral calcineurin inhibitors, or high-potency or oral corticosteroids within the previous 12 months (d) History of idiopathic pulmonary fibrosis, organizing pneumonia (e.g., bronchiolitis obliterans), drug-induced pneumonitis, or idiopathic pneumonitis, or evidence of active pneumonitis;

(e) Treatment with systemic immunosuppressive medication (including, but not limited to, corticosteroids, cyclophosphamide, azathioprine, methotrexate, thalidomide, and anti-TNF-α agents) within 4 weeks or 5 drug-elimination half-lives (whichever is longer) prior to administration of atezolizumab and during treatment with atezolizumab, as described herein with the following exceptions:

(i) Patients who received acute, low-dose systemic immunosuppressant medication or a one-time pulse dose of systemic immunosuppressant medication (e.g., 48 hours of corticosteroids for a contrast allergy); or (ii) Patients who received mineralocorticoids (e.g., fludrocortisone), corticosteroids for chronic obstructive pulmonary disease (COPD) or asthma, or low-dose corticosteroids for orthostatic hypotension or adrenal insufficiency.

Further provided herein is the use (U1) of a combination therapy described herein comprising Compound 1 or a pharmaceutically acceptable salt thereof and atezolizumab for the treatment of lung cancer as described herein. In one embodiment, is a use (U2) of a combination therapy described herein comprising Compound 1 or a pharmaceutically acceptable salt thereof and atezolizumab for the treatment of lung cancer as described herein.

Further provided herein is the use (U3) of a combination therapy described herein comprising Compound 1 or a pharmaceutically acceptable salt thereof and atezolizumab for the treatment of lung cancer as described herein comprising a dosing regimen comprising: (i) administering Compound 1 or a pharmaceutically acceptable salt thereof QD on days 1-21 of a first 21-day cycle; and (ii) administering atezolizumab Q3W on day 1 of the first 21-day cycle.

Further provided herein is the use (U4) of a combination therapy described herein comprising Compound 1 or a pharmaceutically acceptable salt thereof and atezolizumab for the treatment of lung cancer as described herein comprising a dosing regimen comprising: (i) administering about 50-500 mg Compound 1 or a pharmaceutically acceptable salt thereof QD on days 1-21 of a first 21-day cycle; and (ii) administering about 1200 mg atezolizumab Q3W on day 1 of the first 21-day cycle. In one such embodiment, the dosing regimen includes 2 or more cycles as described herein.

Further provided herein is the use (U5) of a combination therapy described herein comprising Compound 1 or a pharmaceutically acceptable salt thereof and atezolizumab for the manufacture of a medicament for the treatment of lung cancer as described herein.

Further provided herein is the use (U6) of a combination therapy described herein comprising Compound 1 or a pharmaceutically acceptable salt thereof and atezolizumab for the manufacture of a medicament for the treatment of lung cancer as described herein comprising a dosing regimen comprising: (i) administering Compound 1 or a pharmaceutically acceptable salt thereof QD on days 1-21 of a first 21-day cycle; and (ii) administering atezolizumab Q3W on day 1 of the first 21-day cycle.

Further provided herein is the use (U7) of a combination therapy described herein comprising Compound 1 or a pharmaceutically acceptable salt thereof and atezolizumab for the manufacture of a medicament for the treatment of lung cancer as described herein comprising a dosing regimen comprising: (i) administering about 50-500 mg Compound 1 or a pharmaceutically acceptable salt thereof QD on days 1-21 of a first 21-day cycle; and (ii) administering about 1200 mg atezolizumab Q3W on day 1 of the first 21-day cycle. In one such embodiment, the dosing regimen includes 2 or more cycles as described herein.

In such embodiments of the uses described herein, the lung cancer can be NSCLC. In another such embodiment of the uses described herein, a patient described herein is diagnosed with NSCLC, adenocarcinoma, squamous-cell lung carcinoma, large-cell lung carcinoma, or SCLC mediated by a $KRas^{G12C}$ mutation.

The development of combination treatments poses challenges including, for example, the selection of agents for combination therapy that may lead to improved efficacy while maintaining acceptable toxicity. One particular challenge is the need to distinguish the incremental toxicity of the combination. In one embodiment of the methods described herein the combination therapy described herein (e.g. Compound 1 or a pharmaceutically acceptable salt thereof and atezolizumab) is administered in a dosing regimen comprising a staggered dosing schedule. In one such embodiment, the patient has a reduced number or grade of adverse events (AEs) comparable to a control (e.g. SOC therapy, treatment with one agent described herein (e.g. Compound 1 or a pharmaceutically acceptable salt thereof or atezolizumab) alone).

It is generally understood that the when an adverse event occurs, four options exist: (1) continue treatment as-is with optional concomitant therapy; (2) adjust the dose of one or more agents in the dosing regiment; (3) suspend administration of one or more agents in the dosing regimen; or (4) discontinue administration of one or more agents in the dosing regimen. In one embodiment, the amount of Compound 1 or a pharmaceutically acceptable salt thereof is not modified. In another embodiment, the amount of atezolizumab administered is not modified. In one embodiment, where the administration of atezolizumab is interrupted, the next administration of Compound 1 or a pharmaceutically acceptable salt thereof occurs on the same day as administration of atezolizumab is resumed. In one embodiment, Compound 1 or a pharmaceutically acceptable salt thereof is administered without food (i.e. a patient should not eat at least 2 hours before and 1 hour after administration).

In one embodiment, a patient described herein experiences gastrointestinal toxicity as an AE at a grade of less than or equal to 2. In one such embodiment, the gastrointestinal toxicity is diarrhea, nausea, or vomiting. In another embodiment, a patient described herein experiences phototoxicity. In such embodiments, the patient should wear sunscreen and protective clothing outdoors.

Patients described herein can also be administered concomitant therapies including: (a) anti-seizure medications or warfarin; (b) oral contraceptives or other allowed maintenance therapy; (c) anti-emetics and anti-diarrheal medications provided that such medications should not be administered prophylactically before initial treatment with study drug; (d) pain medications administered per standard clinical practice; (e) bisphosphonate and denosumab therapy for bone metastases or osteopenia/osteoporosis; and/or (f) multivitamins, calcium, and vitamins C, D, and E supplements.

Patients described herein may not concomitantly take therapies including (1) Strong/moderate CYP3A4 inhibitors (e.g. atazanavir, ritonavir, indinavir, nelfinavir, saquinavir, clarithromycin, telithromycin, erythromycin, troleandomycin, fluconazole, itraconazole, ketoconazole, voriconazole, posaconazole, aprepitant, conivaptan, fluvoxamine, diltiazem, nefazodone, mibefradil, verapamil, and grapefruit juice or grapefruit supplements) or (2) Strong/moderate CYP3A4 inducers (e.g. rifampin, carbamazepine, phenytoin, oxcarbazepine, phenobarbital, efavirenz, nevirapine, etravirine, modafinil, hyperforin (St. John's Wort), and cyproterone).

In another embodiment, patients described herein are not administered any of the following therapies:
(a) Any other investigational therapy (excluding Compound 1 or a pharmaceutically acceptable salt thereof or atezolizumab) within 3 weeks or five half-lives prior to administration of a combination therapy described herein, whichever is shorter, or during such treatment;
(b) Concomitant therapy intended for the treatment of cancer whether approved by the FDA or experimental, including chemotherapy, radiotherapy, immunotherapy, biologic therapy, herbal therapy, or hormonal therapy except for the following:
  (i) Hormonal therapy with gonadotropin-releasing hormone (GnRH) agonists or antagonists for endocrine sensitive cancers (e.g., prostate, endometrial, hormone receptor-positive breast cancer);
  (ii) Hormone replacement therapy or oral contraception;

(c) Radiotherapy for unequivocal progressive disease with the exception of new brain metastases in the setting of systemic response as follows: patients who have demonstrated control of their systemic disease (defined as having received clinical benefit [i.e., a PR, CR, or SD for A months]), but who have developed brain metastases that are treatable with radiation, will be allowed to continue to receive therapy with Compound 1 or a pharmaceutically acceptable salt thereof during the study until they either experience systemic progression of their disease and/or further progression in the brain (based on investigator assessments).
(d) Quinidine or other anti-arrhythmic agents;
(e) Initiation or increased dose of hematopoietic colony-stimulating factors (CSFs; e.g., granulocyte CSF; filgrastim, granulocyte/macrophage CSF; sargramostim, pegfilgrastim, erythropoietin, darbepoetin, and thrombopoietin) from 7 days before Cycle 1, Day 1;
(f) Live, attenuated vaccines (e.g., FluMist®) within 4 weeks prior to administration of a combination therapy described herein, and for 5 months after the final dose of atezolizumab;
(g) Systemic immunostimulatory agents (including, but not limited to, interferons and IL 2) within 4 weeks or 5 drug-elimination half-lives (whichever is longer) prior to, and during, administration of a combination therapy described herein.

Patient Stratification

In one embodiment of such methods, the patient is diagnosed with a cancer cancer comprising a $KRas^{G12C}$ mutation as described herein. In another such embodiment, the patient is diagnosed as having a cancer expressing PD-L1. Such diagnoses can be made from one or more samples taken from the patient and test as described herein. In one embodiment, the sample is a tumor sample taken from the subject. In one such embodiment, the sample is taken before administration of any therapy described herein. In another such embodiment, the sample is taken before administration of at least one agent described herein. In some embodiments, tumor samples can be taken at specified intervals during treatment with a combination therapy described herein to assess treatment.

Determining whether a tumor or cancer comprises a $KRas^{G12C}$ mutation can be undertaken by assessing the nucleotide sequence encoding the K-Ras protein, by assessing the amino acid sequence of the K-Ras protein, or by assessing the characteristics of a putative K-Ras mutant protein. The sequence of wild-type human K-Ras (e.g. Accession No. NP203524) is known in the art. In one such embodiment, a sample from a patient described herein is assessed for a $KRas^{G12C}$ mutation using, for example, immunohistochemistry (IHC) or NGS sequencing.

The expression of PD-L1 may be assessed in a patient treated according to any of the methods and compositions for use described herein. The methods and compositions for use may include determining the expression level of PD-L1 in a biological sample (e.g., a tumor sample) obtained from the patient. In other examples, the expression level of PD-L1 in a biological sample (e.g., a tumor sample) obtained from the patient has been determined prior to initiation of treatment or after initiation of treatment. PD-L1 expression may be determined using any suitable approach. For example, PD-L1 expression may be determined as described in U.S. patent application Ser. Nos. 15/787,988 and 15/790,680. Any suitable tumor sample may be used, e.g., a formalin-fixed and paraffin-embedded (FFPE) tumor sample, an archival tumor sample, a fresh tumor sample, or a frozen tumor sample.

For example, PD-L1 expression may be determined in terms of the percentage of a tumor sample comprised by tumor-infiltrating immune cells expressing a detectable expression level of PD-L1, as the percentage of tumor-infiltrating immune cells in a tumor sample expressing a detectable expression level of PD-L1, and/or as the percentage of tumor cells in a tumor sample expressing a detectable expression level of PD-L1. It is to be understood that in any of the preceding examples, the percentage of the tumor sample comprised by tumor-infiltrating immune cells may be in terms of the percentage of tumor area covered by tumor-infiltrating immune cells in a section of the tumor sample obtained from the patient, for example, as assessed by IHC using an anti-PD-L1 antibody (e.g., the SP142 antibody). Any suitable anti-PD-L1 antibody may be used, including, e.g., SP142 (Ventana), SP263 (Ventana), 22C3 (Dako), 28-8 (Dako), E1L3N (Cell Signaling Technology), 4059 (ProSci, Inc.), h5H1 (Advanced Cell Diagnostics), and 9A11. In some examples, the anti-PD-L1 antibody is SP142. In other examples, the anti-PD-L1 antibody is SP263.

In some examples, a tumor sample obtained from the patient has a detectable expression level of PD-L1 in less than 1% of the tumor cells in the tumor sample, in 1% or more of the tumor cells in the tumor sample, in from 1% to less than 5% of the tumor cells in the tumor sample, in 5% or more of the tumor cells in the tumor sample, in from 5% to less than 50% of the tumor cells in the tumor sample, or in 50% or more of the tumor cells in the tumor sample.

In some examples, a tumor sample obtained from the patient has a detectable expression level of PD-L1 in tumor-infiltrating immune cells that comprise less than 1% of the tumor sample, more than 1% of the tumor sample, from 1% to less than 5% of the tumor sample, more than 5% of the tumor sample, from 5% to less than 10% of the tumor sample, or more than 10% of the tumor sample.

In some examples, tumor samples may be scored for PD-L1 positivity in tumor-infiltrating immune cells and/or in tumor cells according to the criteria for diagnostic assessment shown in Table A and/or Table B, respectively.

TABLE A

Tumor-infiltrating immune cell (IC) IHC diagnostic criteria

| PD-L1 Diagnostic Assessment | IC Score |
|---|---|
| Absence of any discernible PD-L1 staining OR Presence of discernible PD-L1 staining of any intensity in tumor-infiltrating immune cells covering <1% of tumor area occupied by tumor cells, associated intratumoral stroma, and contiguous peri-tumoral desmoplastic stroma | IC0 |
| Presence of discernible PD-L1 staining of any intensity in tumor-infiltrating immune cells covering ≥1% to <5% of tumor area occupied by tumor cells, associated intratumoral stroma, and contiguous peri-tumoral desmoplastic stroma | IC1 |
| Presence of discernible PD-L1 staining of any intensity in tumor-infiltrating immune cells covering ≥5% to <10% of tumor area occupied by tumor cells, associated intratumoral stroma, and contiguous peri-tumoral desmoplastic stroma | IC2 |
| Presence of discernible PD-L1 staining of any intensity in tumor-infiltrating immune | IC3 |

TABLE A-continued

Tumor-infiltrating immune cell (IC) IHC diagnostic criteria

| PD-L1 Diagnostic Assessment | IC Score |
|---|---|
| cells covering ≥10% of tumor area occupied by tumor cells, associated intratumoral stroma, and contiguous peri-tumoral desmoplastic stroma | |

TABLE B

Tumor cell (TC) IHC diagnostic criteria

| PD-L1 Diagnostic Assessment | TC Score |
|---|---|
| Absence of any discernible PD-L1 staining OR Presence of discernible PD-L1 staining of any intensity in <1% of tumor cells | TC0 |
| Presence of discernible PD-L1 staining of any intensity in ≥1% to <5% of tumor cells | TC1 |
| Presence of discernible PD-L1 staining of any intensity in ≥5% to <50% of tumor cells | TC2 |
| Presence of discernible PD-L1 staining of any intensity in ≥50% of tumor cells | TC3 |

Also provided herein are methods of inhibiting tumor growth or producing tumor regression in a patient described herein by administering a combination therapy described herein. In one embodiment provided herein is a method of inhibiting tumor growth in a patient having lung described herein by administering a combination therapy comprising administering Compound 1 or a pharmaceutically acceptable salt thereof and atezolizumab in one or more 21-day cycles as described herein.

In one embodiment provided herein is a method of producing or improving tumor regression in a patient having a lung cancer described herein by administering a combination therapy comprising administering Compound 1 or a pharmaceutically acceptable salt thereof and atezolizumab in one or more 21-day cycles as described herein.

Kits

The combination therapies described herein can be provided as a kit comprising one or more of the agents described herein for administration. In one embodiment, the kit includes Compound 1 or a pharmaceutically acceptable salt thereof (e.g. Compound 1 adipate) for administration in combination with atezolizumab as described herein. In another embodiment, the kit includes Compound 1 or a pharmaceutically acceptable salt thereof (e.g. Compound 1 adipate) packaged together with atezolizumab, where the kit comprises separate formulated dosages of each agent.

Also provided herein is an article of manufacture or a kit comprising Compound 1 or a pharmaceutically acceptable salt thereof (e.g. Compound 1 adipate) and a PD-L1 binding antagonist (e.g., atezolizumab). In some instances, the article of manufacture further comprises package insert comprising instructions for using the PD-L1 binding antagonist to treat or delay progression of lung cancer. In one such embodiment, the lung cancer in NSCLS. In one embodiment, the article of manufacture further comprises package insert comprising instructions for using atezolizumab in combination with Compound 1 or a pharmaceutically acceptable salt thereof (e.g. Compound 1 adipate) to treat or delay progression of NSCLC in a patient.

In some instances, the PD-L1 binding antagonist (e.g., atezolizumab) and Compound 1 or a pharmaceutically acceptable salt thereof (e.g. Compound 1 adipate) are in the same container or separate containers. Suitable containers include, for example, bottles, vials, bags and syringes. The container may be formed from a variety of materials such as glass, plastic (such as polyvinyl chloride or polyolefin), or metal alloy (such as stainless steel or hastelloy). In some instances, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some instances, the article of manufacture further includes one or more of another agent (e.g., an additional chemotherapeutic agent or anti-neoplastic agent). Suitable containers for the one or more agents include, for example, bottles, vials, bags and syringes.

Any of the articles of manufacture or kits described herein may include instructions to administer Compound 1 or a pharmaceutically acceptable salt thereof (e.g. Compound 1 adipate) and/or the PD-L1 binding antagonist (e.g., atezolizumab) to a patient in accordance with any of the methods described herein.

Biomarkers

In one embodiment, the alkylation of $KRas^{G12C}$ by Compound 1 or a pharmaceutically acceptable salt thereof is measured in the patient. In one such embodiment, the measurement is performed using a sample and tested for alkylation of $KRas^{G12C}$ as provided herein. In another embodiment, assessment of ctDNA biomarkers (e.g., $KRas^{G12C}$) from peripheral blood is performed. In still another embodiment, alterations in DNA, RNA, and protein, including DNA mutation status and copy number; RNA expression levels, localization and splicing; and protein expression (e.g., PD-L1) are determined.

In one embodiment, modulation of KRAS/MAPK target genes (e.g., DUSP6, SPRY4), pathway components (e.g., pERK, pS6), and related biomarkers (e.g., Ki67) through analysis of paired pre-treatment and on-treatment fresh tumor biopsies is performed.

EMBODIMENTS

Provided below are exemplary embodiments of the invention.

Embodiment No. 1: A combination therapy comprising:
(a) Compound 1

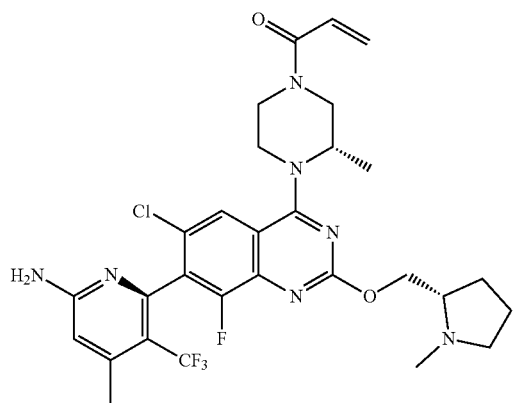

or a pharmaceutically acceptable salt thereof and;

(b) a PD-L1 binding antagonist.

Embodiment No. 2: The combination therapy of embodiment 1, wherein the PD-L1 binding antagonist is an anti-PD-L1 antibody.

Embodiment No. 3: The combination therapy of embodiment 1 or 2, wherein the anti-PD-L1 antibody is atezolizumab.

Embodiment No. 4: The combination therapy of any one of embodiments 1-3, wherein Compound 1 is an adipate salt thereof.

Embodiment No. 5: The combination of any one of embodiments 1-4, wherein Compound 1 or a pharmaceutically acceptable salt thereof is administered QD on days 1-21 of a first 21-day cycle and atezolizumab administered Q3W on day 1 of the first 21-day cycle.

Embodiment No. 6: The combination therapy of any one of embodiments 1-5, wherein Compound 1 or a pharmaceutically acceptable salt thereof is administered orally as a tablet or capsule.

Embodiment No. 7: The combination therapy of any one of embodiments 1-6, wherein Compound 1 or a pharmaceutically acceptable salt thereof is administered at an amount of about 50 mg-500 mg.

Embodiment No. 8: The combination therapy of any one of embodiments 1-7, wherein Compound 1 or a pharmaceutically acceptable salt thereof is administered at an amount of about 5 mg, 25 mg, 50 mg, 100 mg, 150 mg, 200 mg, 250 mg, 300 mg, 400 mg or 500 mg.

Embodiment No. 9: The combination therapy of any one of embodiments 3-8, wherein atezolizumab is administered at an amount of about 1000 mg to about 1400 mg Q3W.

Embodiment No. 10: The combination therapy of embodiment 9, wherein atezolizumab is administered at an amount of about 840 mg Q2W, about 1200 mg Q3W, or about 1680 mg of Q4W.

Embodiment No. 11: The combination therapy of embodiment 9 or 10, wherein atezolizumab is administered to the patient intravenously at a dose of about 1200 mg Q3W.

Embodiment No. 12: The combination therapy of any one of embodiment 1-11 for use in lung cancer comprising a $KRas^{G12C}$ mutation.

Embodiment No. 13: The combination therapy of embodiment 12, wherein the lung cancer is non-small cell lung carcinoma (NSCLC).

Embodiment No. 14: A combination therapy comprising:
(a) Compound 1 or a pharmaceutically acceptable salt thereof administered QD on days 1-21 of a first 21-day cycle and;
(b) atezolizumab administered Q3W on day 1 of the first 21-day cycle.

Embodiment No. 15: The combination therapy of embodiment 14, wherein Compound 1 or a pharmaceutically acceptable salt thereof is administered QD at an amount of about 50 mg-500 mg on days 1-21 of a first 21-day cycle and atezolizumab is administered Q3W at an amount of about 1200 mg on day 1 of the first 21-day cycle.

Embodiment No. 16: A method of treating lung cancer mediated by a $KRas^{G12C}$ mutation in a patient having such a lung cancer, the method comprising administering an effective amount of a combination therapy comprising:
(a) Compound 1 or a pharmaceutically acceptable salt thereof and;
(b) a PD-L1 binding antagonist.

Embodiment No. 17: The method of embodiment 16, wherein the PD-L1 binding antagonist is an anti-PD-L1 antibody.

Embodiment No. 18: The method of embodiment 16 or 17, wherein the anti-PD-L1 antibody is atezolizumab.

Embodiment No. 19: The method of any one of embodiments 16-18, wherein Compound 1 is an adipate salt thereof.

Embodiment No. 20: The method of any one of embodiments 18-19, wherein Compound 1 or a pharmaceutically acceptable salt thereof is administered QD on days 1-21 of a first 21-day cycle and atezolizumab administered Q3W on day 1 of the first 21-day cycle.

Embodiment No. 21: The method of any one of embodiments 16-20, wherein Compound 1 or a pharmaceutically acceptable salt thereof is administered orally as a tablet or capsule.

Embodiment No. 22: The method of any one of embodiments 16-21, wherein Compound 1 or a pharmaceutically acceptable salt thereof is administered at an amount of about 50 mg-500 mg.

Embodiment No. 23: The method of any one of embodiments 16-22, wherein Compound 1 or a pharmaceutically acceptable salt thereof is administered at an amount of about 5 mg, 25 mg, 50 mg, 100 mg, 150 mg, 200 mg, 250 mg, 300 mg, 400 mg or 500 mg.

Embodiment No. 24: The method of any one of embodiments 18-23, wherein atezolizumab is administered at an amount of about 1000 mg to about 1400 mg Q3W.

Embodiment No. 25: The method of any one of embodiments 18-24, wherein atezolizumab is administered at an amount of about 840 mg Q2W, about 1200 mg Q3W, or about 1680 mg of Q4W.

Embodiment No. 26: The method of any one of embodiments 18-25, wherein atezolizumab is administered to the patient intravenously at a dose of about 1200 mg Q3W.

Embodiment No. 27: The combination therapy of any one of embodiment 16-26, wherein the lung cancer is NSCLC.

Embodiment No. 28: The combination therapy of any one of embodiment 16-26, wherein the lung cancer is adenocarcinoma, squamous-cell lung carcinoma or large-cell lung carcinoma.

Embodiment No. 29: A method of treating NSCLC comprising a KRas$^{G12C}$ mutation in a patient having such a cancer, the method comprising administering to the patient an effective amount of a combination therapy comprising:
(a) Compound 1 or a pharmaceutically acceptable salt thereof, wherein Compound 1 or a pharmaceutically acceptable salt thereof is administered QD on days 1-21 of a first 21-day cycle and;
(b) atezolizumab administered Q3W on day 1 of the first 21-day cycle.

Embodiment No. 30: The method of embodiment 29, wherein:
(i) Compound 1 or a pharmaceutically acceptable salt thereof is administered at an amount of about 50 mg-500 mg QD on days 1-21 of the first 21-day cycle; and
(ii) atezolizumab is administered Q3W at an amount of 1200 mg on day 1 of the first 21-day cycle.

Embodiment No. 31: The method of any one of embodiments 18-30, wherein atezolizumab is administered after administration of Compound 1 or a pharmaceutically acceptable salt thereof.

Embodiment No. 32: A method of treating NSCLC in a patient having NSCLC, the method comprising administering to the patient a treatment regimen comprising an effective amount of Compound 1 or a pharmaceutically acceptable salt thereof and a PD-L1 binding antagonist.

Embodiment No. 33: The method of embodiment 32, wherein Compound 1 is an adipate salt.

Embodiment No. 34: The method of embodiment 32 or embodiment 33, wherein the PD-L1 binding antagonist is atezolizumab.

Embodiment No. 35: The method of any one of embodiments 32-34, wherein:
(i) Compound 1 or a pharmaceutically acceptable salt thereof is administered at an amount of about 50 mg-500 mg QD on days 1-21 of the first 21-day cycle; and
(ii) atezolizumab is administered Q3W at an amount of 1200 mg on day 1 of the first 21-day cycle.

Embodiment No. 36: The method of any one of embodiments 16-35, wherein the patient is diagnosed as not having a mutation selected from the group consisting of sensitizing EGFR mutations, ALK rearrangement, ROS1 rearrangement, BRAF V600E mutation, NTRK fusions, and RET fusions, or a combination thereof.

Embodiment No. 37: Use (U1) of a combination therapy comprising Compound 1 or a pharmaceutically acceptable salt thereof and atezolizumab for the treatment of lung cancer as described herein.

Embodiment No. 38: The use of embodiment 37, further comprising a dosing regimen comprising: (i) administering Compound 1 or a pharmaceutically acceptable salt thereof QD on days 1-21 of a first 21-day cycle; and (ii) administering atezolizumab Q3W on day 1 of the first 21-day cycle Embodiment No. 39: The use of embodiment 38, further comprising (i) administering about 50-500 mg Compound 1 or a pharmaceutically acceptable salt thereof QD on days 1-21 of the first 21-day cycle; and (ii) administering about 1200 mg atezolizumab Q3W on day 1 of the first 21-day cycle.

Embodiment No. 40: Use (U5) of a combination therapy comprising Compound 1 or a pharmaceutically acceptable salt thereof and atezolizumab for the manufacture of a medicament for the treatment of lung cancer.

Embodiment No. 41: The use of embodiment 40, further comprising: (i) administering Compound 1 or a pharmaceutically acceptable salt thereof QD on days 1-21 of a first 21-day cycle; and (ii) administering atezolizumab Q3W on day 1 of the first 21-day cycle.

Embodiment No. 42: The use of embodiment 41, further comprising: (i) administering about 50-500 mg Compound 1 or a pharmaceutically acceptable salt thereof QD on days 1-21 of a first 21-day cycle; and (ii) administering about 1200 mg atezolizumab Q3W on day 1 of the first 21-day cycle. In one such embodiment, the dosing regimen includes 2 or more cycles as described herein.

Embodiment No. 43: The method of any one of embodiments 16-36 or use of any one of embodiments 37-42, wherein the alkylation of KRas$^{G12C}$ by Compound 1 or a pharmaceutically acceptable salt thereof is measured in the patient.

The following Examples are presented by way of illustration, not limitation.

EXAMPLES

Example 1: Preclinical Synergy

Nonclinical data combining the adipate salt of Compound 1 with anti-PD-L1 therapy also showed a synergistic effect with greater tumor reduction in mice compared to the use of either treatment alone.

The combination of the adipate salt of Compound 1 with anti-PD-L1 monoclonal antibody (mAb) was assessed in the CRISPR-engineered CT26.KRAS12C-Clone #12:B2G9 mouse colorectal (CRC) syngeneic tumor model.

Test Agents. The adipate salt of Compound 1 was in a solution at a concentration of 7.5 mg/mL in 0.5% (w/v) methylcellulose. Anti-PD-L1 mAbs (Mu IgG1 anti-PD-L1 (6E11); hereafter referred to as anti-PD-L1) was in a solution in Histidine Buffer #8 (20 nM Histidine Acetate, 240 nM Sucrose, 0.02% Tween 20™, pH 5.5). The oral-dosed vehicle control was 0.5% (w/v) methylcellulose. Test agents were stored in a refrigerator set to maintain a temperature range of 4° C.-7° C. All treatments and vehicle control dosing solutions were prepared once a week for three weeks.

Female Balb/c mice that were 9-10 weeks old were obtained from Charles River Laboratory (Hollister, CA) weighing an average of 22 g. Only animals that appeared to be healthy and that were free of obvious abnormalities were used for the study. *Mus musculus* colon carcinoma CT26 cells were obtained from the American Type Culture Collection (Rockville, MD). CT26.KRAS12C-Clone #12:B2G9 is derived from CRISPR knock-in of G12C in CT26 cells. Cells were cultured in vitro, harvested in log-phase growth, and resuspended in Hank's Balanced Salt Solution (HBSS) containing Matrigel (BD Biosciences; San Jose, CA) at a 1:1 ratio. The cells were then implanted subcutaneously in the right lateral thorax of 70 Balb/c mice. Each mouse was injected with $0.1 \times 10^6$ cells in a volume of 100 µL. Tumors were monitored until they reached a mean tumor volume of 159-228 mm$^3$. Mice were distributed into six groups based on tumor volumes with n=8 mice per group. The mean tumor volume across all six groups was 198 mm$^3$ at the initiation of dosing.

Mice were given vehicles (100 µL 0.5% MC and 100 µL 0.5% MCT), 50 mg/kg of the adipate salt of Compound 1 (expressed as free-base equivalents). The MC vehicle and adipate salt of Compound 1 were administered on QD orally (PO) by gavage for 21 days in a volume of 100 µL. The isotope control mAbs and anti-PD-L1 mAbs were administered intravenously (IV) at 10 mg/kg for the first dose, and then dosed intraperitoneally (IP) at 5 mg/kg for subsequent doses on a twice weekly (BIW) schedule.

Tumor sizes and mouse body weights were recorded twice weekly over the course of the study. Mice were promptly euthanized when tumor volume exceeded 2000 mm$^3$ or if body weight loss was 20% of their starting weight.

| Treatment | Dose level (mg/kg)$^a$ | Route | Schedule | Days of Dosing | Dose Conc. (mg/mL)$^a$ | Dose Volume (mL/kg) |
|---|---|---|---|---|---|---|
| Vehicle | 0, 10/5 | PO | QD, BIW | 21 | 0, 2.5 | 4, 4 |
| Adipate Salt Compound 1 | 30 | PO | PO | 21 | 7.5 | 4 |
| Anti-PD-L1 (6E11) | 10/5 | PO | BIW | 21 | 2.5 | 4 |
| Compound 1 + Anti-PD-L1 | 30 + 10/5 | PO | QD, BIW | 21 | 7.5, 2.5 | 4, 4 |

Dose Preparation and Tumor and Body Weight Measurement. All concentrations were calculated based on a mean body weight of 25 g for the nude mouse strain used in this study. Tumor volumes were measured in two dimensions (length and width) using Ultra Cal-IV calipers (model 54-10-111; Fred V. Fowler Co.; Newton, MA) and analyzed using Excel, version 14.2.5 (Microsoft Corporation; Redmond WA). The tumor volume was calculated with the following formula:

Tumor size(mm$^3$)=(longer measurement×shorter measurement$^2$)×0.5

Anti-tumor responses were noted with partial responses (PRs) being defined as a >50% decrease from the initial tumor volume and complete responses (CRs) being defined as a 100% decrease in tumor volume.

Animal body weights were measured using an Adventure Pro AV812 scale (Ohaus Corporation; Pine Brook, NJ). Percent weight change was calculated using the following formula:

Body weight change(%)=[(current body weight/initial body weight)−1]×100]

Estimates of efficacy were obtained by calculating the percent difference between the daily average baseline-corrected AUC of the relevant group fits on the original (i.e., untransformed) scale over a common time period.

Figure 1B:
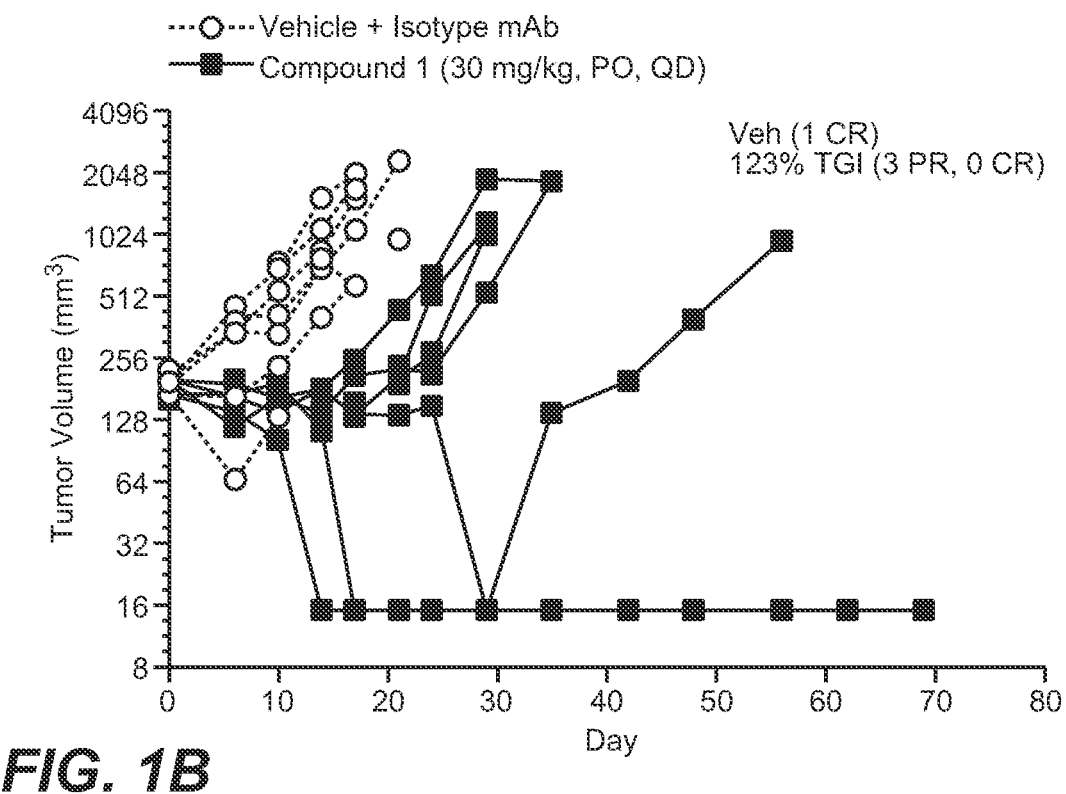
FIG. 1B illustrates the effect SA dose of the adipate salt of Compound 1 described herein in the same model as FIG. 1A.
Figure 1C:
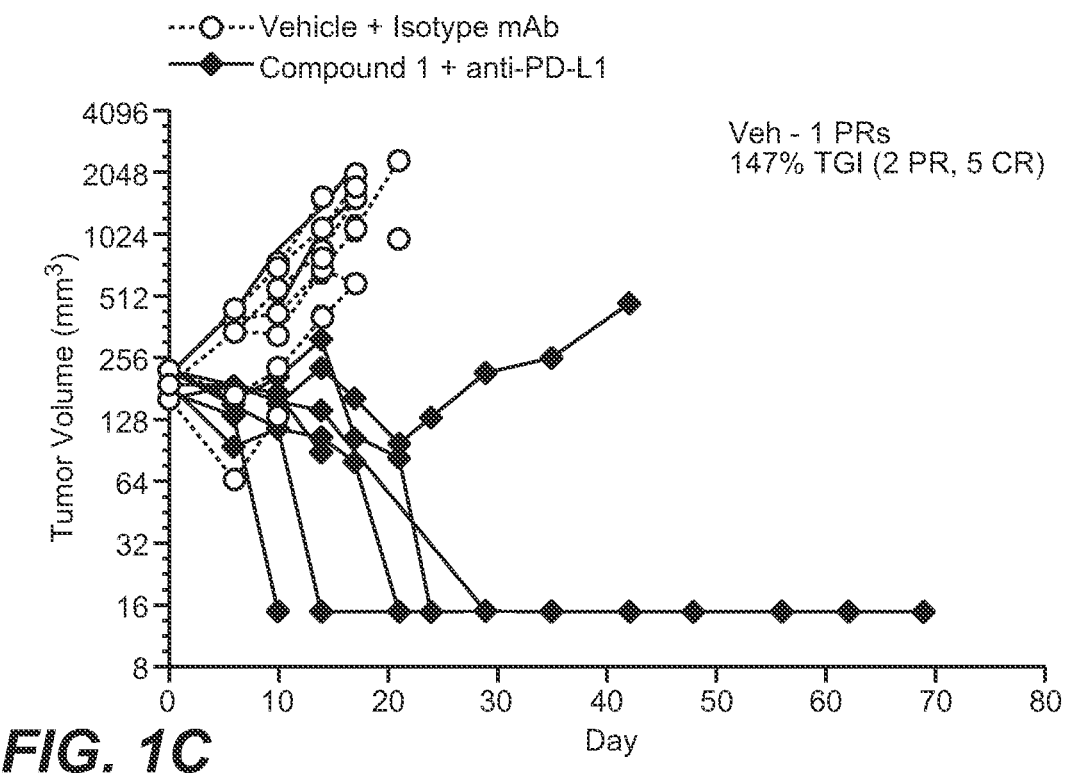
FIG. 1C illustrates the effect of dosing the adipate salt of Compound 1 in combination with the anti-PD-L1 mAb.
Figure 2:
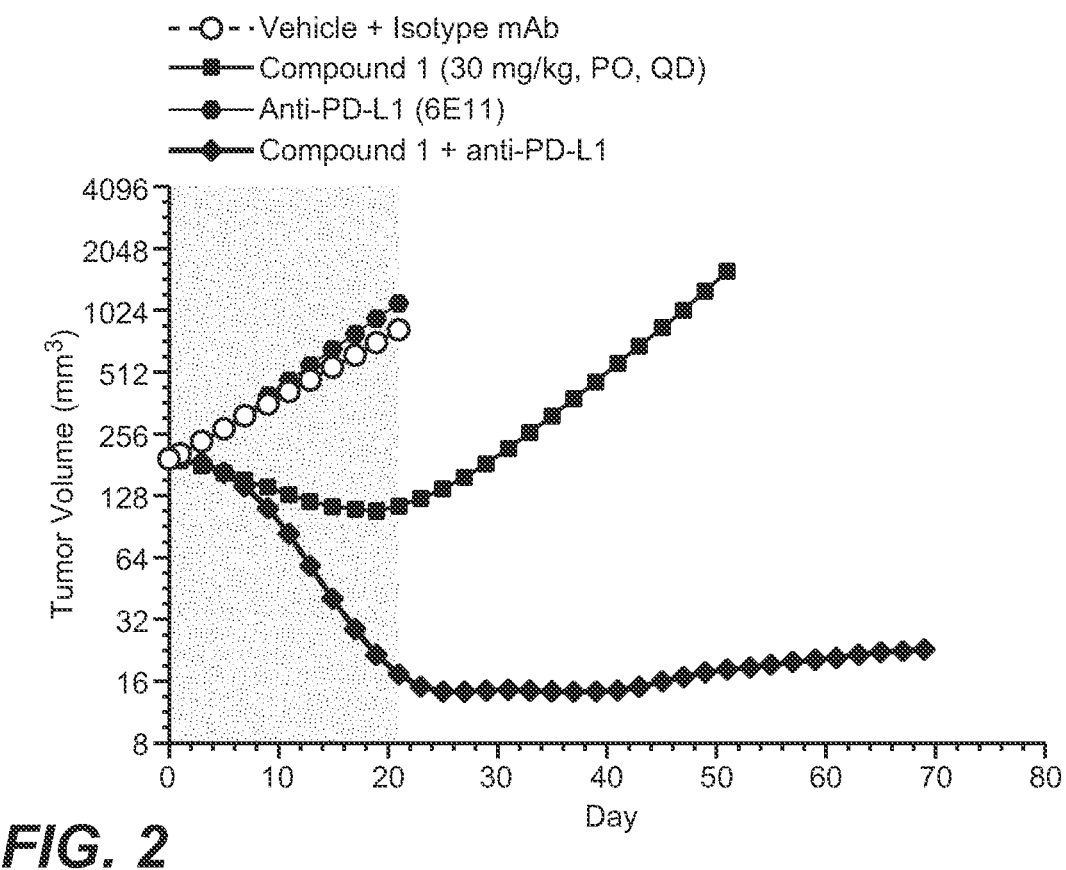
FIG. 2 illustrates Tumor Volumes of CT26.KRAS12C-Clone #12:B2G9 Syngeneic Colorectal (CRC) Tumor-Bearing Balb/c Mice Treated With the adipate salt of Compound 1 Dosed Alone or in Combination with Anti-PD-L1.
Figure 3:
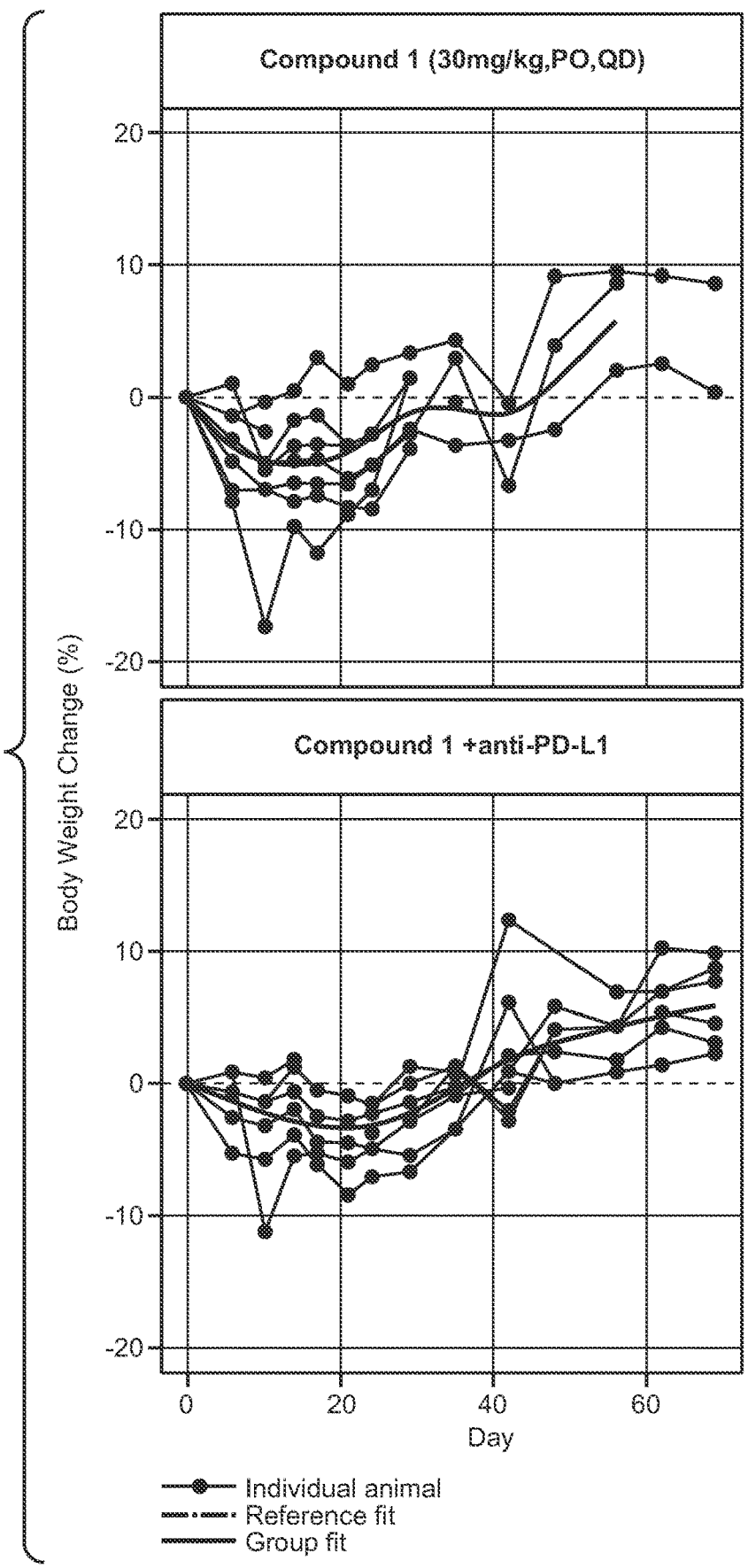
FIG. 3 illustrates Individual Body Weight Data of CT26.KRAS12C-Clone #12:B2G9 Syngeneic Colorectal (CRC) Tumors in Balb/c Mice Treated with the adipate salt of Compound 1 Dosed Alone and in Combination with Anti-PD-L1.
Figure 4:
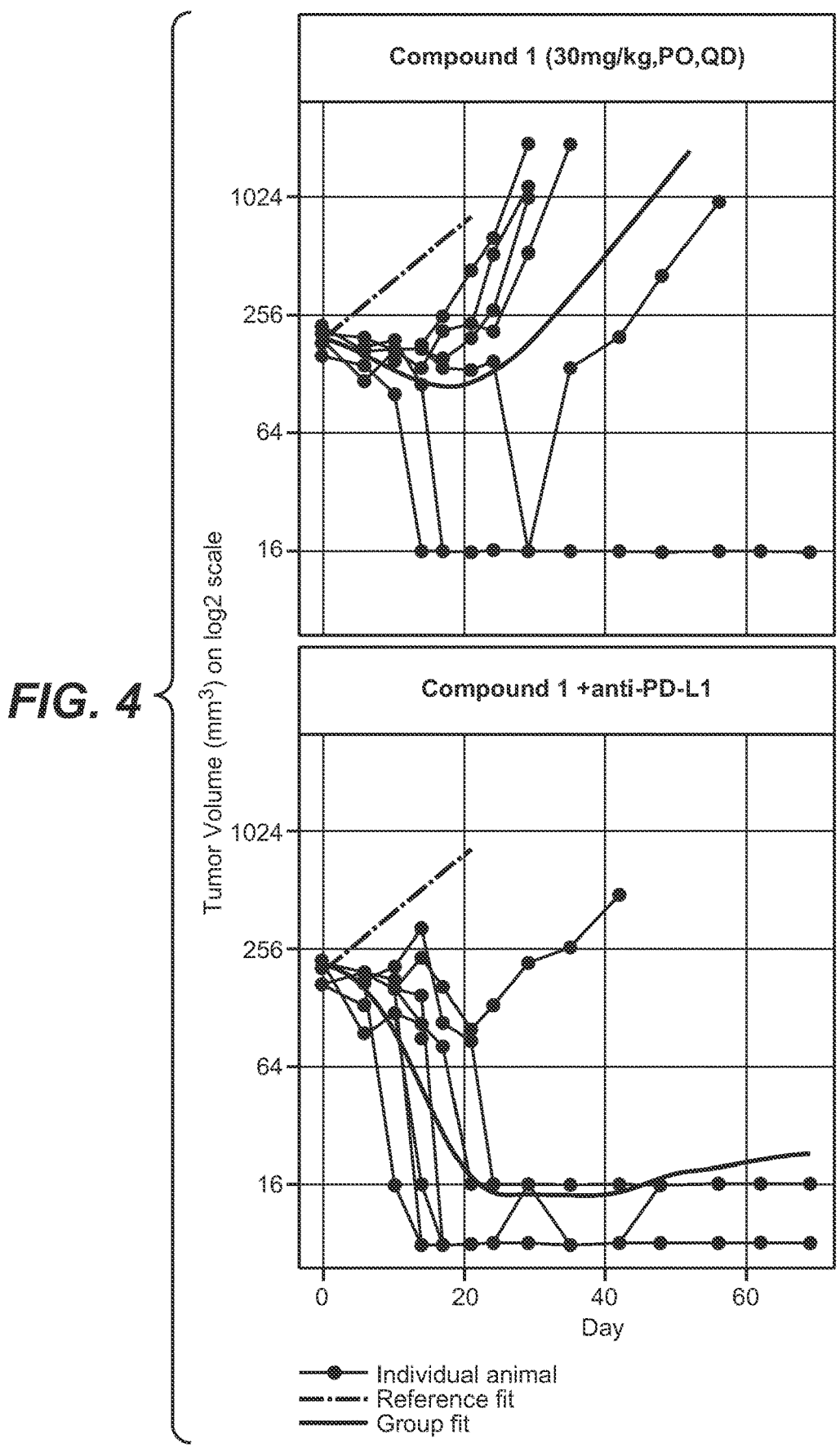
FIG. 4 shows Individual Tumor Volume Data of CT26.KRAS12C-Clone #12:B2G9 Syngeneic Colorectal (CRC) Tumors in Balb/c Mice Treated with the adipate salt of Compound 1 Dosed Alone or in Combination with Anti-PD-L1.

Anti-tumor efficacy was assessed in nude mice bearing human NCI-H2122 NSCLC xenografts following treatment with the adipate salt of Compound 1 (30 mg/kg, PO, QD) alone compared to anti-PD-L1 (10 mg/kg, IV, first dose, then 5 mg/kg, IP, BIW). The single agent (SA) treatments resulted in tumor growth inhibition (TGI). The SA treatment with the adipate salt of Compound 1 resulted in 123% TGI with ⅜ partial responses (PRs). The SA treatment with anti-PD-L1 resulted in −38% TGI with ⅛ PRs, relative to vehicle controls (see FIG. 1, FIG. 4). The combination of the adipate salt of Compound 1 and anti-PD-L1 resulting in 147% TGI with ⅔ PRs and ⅝ CRs (see FIG. 1 and FIG. 2). All treatments were well tolerated, as determined by the percent change in body weights (See FIG. 4).

Summary of Anti-Tumor Activity of the adipate salt of Compound 1 Dosed Alone or in Combination with Anti-PD-L1 in CT26.KRAS12C-Clone #12:B2G9 Syngeneic Colorectal (CRC) Tumors in Balb/c Mice:

| Treatment | Dose Levels (mg/kg) | TI | PR | CR | % TGI (estimated) | % TGI (lower CI) | % TGI (upper CI) |
|---|---|---|---|---|---|---|---|
| Vehicle | 0, 10/5 | 8/8 | 0 | 1 | 0 | 0 | 0 |
| adipate salt Compound 1 | 30 | 8/8 | 3 | 0 | 123 | 67 | 234 |
| Anti-PD-L1 (6E11) | 10/5 | 8/8 | 1 | 0 | −38 | −943 | 75 |
| Compound 1 + Anti-PD-L1 | 30 + 10/5 | 8/8 | 2 | 5 | 147 | 109 | 346 |

CI = confidence interval; CR = complete response; PR = partial response; QD = once daily; TI = tumor incidence.

Notes:
% TGI = percent of tumor growth inhibition based on AUC (see Data Analysis section for equation).

Combination anti-tumor efficacy studies were performed in the CT26.KRAS12C-Clone #12:B2G9 syngeneic CRC tumor model. Consistent with data generated with checkpoint inhibitors in the CT26 tumor model (REF), single agent anti-PD-L1 failed to inhibit tumor growth (−38% TGI, ⅛ PR). Single agent treatment with the adipate salt of Compound 1 regressed tumors (123% TGI) with ⅜ PRs. In contrast, combination of the adipate salt of Compound 1 with anti-PD-L1 resulted in improved tumor regression (147% TGI) with the majority of tumors responding with ⅖ PRs and ⅝ CRs with ⅞ (87.5%) showing durable responses through day 69. (See FIG. 1 and FIG. 2). These data demonstrate that combining the adipate salt of Compound 1 with checkpoint inhibition, such as anti-PD-L1, can lead to improved anti-tumor activity in the CT26.KRAS12C mutant syngeneic tumor model.

Example 2

Initial systemic treatment options for advanced stage or metastatic NSCLC (without known oncogenic drivers that have available targeted therapies) include PD-1/PD-L1 inhibitors with or without chemotherapy (Gong, et al. J Immunother Cancer 2018; 6:8). Subsequent treatment options may include platinum-containing chemotherapy combinations followed by single-agent chemotherapy with limited duration of disease control (NCCN Guidelines Version 2.2020 (a). Non-Small Cell Lung Cancer). Although a minority of patients achieve long-term disease control, in general, advanced stage or metastatic NSCLC remains an incurable disease. Recent data suggest that KRAS mutation status may be associated with response to single-agent PD-1 inhibitor therapy and that chemotherapy plus a PD-1 inhibitor may be effective regardless of KRAS mutation status (Gadgeel S, et al. Annals of Oncology, Volume 30, Issue Supplement_11, December 2019 ESMO Immuno-Oncology Congress 2019. LBA5; Herbst R S, et al. Ann Oncol 30, Issue Supplement_11, December 2019. ESMO Immuno-Oncology Congress 2019. LBA4).

KRAS is the most frequently mutated oncogene in up to 25% of cancers and is associated with resistance to select standard-of-care therapies and overall poor prognosis. Although selective inhibitors have been developed as anti-cancer therapy to target other nodes in the RAS/MAPK pathway, the KRAS oncoprotein was considered undruggable until the recent discovery of the switch II pocket (Ostrem, et al. Nature 2013; 503:548-51). With this finding, covalent small molecule inhibitors aimed at targeting KRAS, and specifically the $KRAS^{G12C}$ mutation, are being evaluated in early clinical development.

Other $KRAS^{G12C}$ inhibitors. AMG 510 (sotorasib) is a small molecule that irreversibly inhibits $KRAS^{G12C}$ by locking it in its inactive GDP-bound state. AMG-510 is currently being investigated in ongoing clinical studies. Patients in those studies received a median of 3 (range, 0 to 11) prior lines of anti-cancer therapies for metastatic disease before entering the study. Overall, treatment-related adverse events were reported in 56.6% of patients; 11.6% of patients experienced a treatment-related Grade 3 or 4 event, and 1.6% of patients experienced a treatment-related serious adverse event. Grade 3 events occurring in more than one patient included ALT increase, diarrhea, anemia, AST increase, and alkaline phosphatase increase. One patient experienced Grade 4 treatment-related ALT increase, and one patient discontinued AMG 510 due to Grade 3 treatment-related ALT and AST increase. While anti-tumor activity was reported, adverse events associated with AMG-510 exist. Patients had a confirmed objective response in 32.2% of patients with NSCLC and the median duration of response was 10.9 months (range, 1.1+ to 13.6) in patients. Median PFS was reported to be 6.3 months (range, 0.0+ to 14.9+) in patients with NSCLC (Hong et al. New Eng J Med 2020; 383:1207-17).

MRTX849 is a mutant-selective small molecule $KRAS^{G12C}$ inhibitor being evaluated in a clinical study of patients with advanced solid tumors with the $KRAS^{G12C}$ mutation. Data from a total of 17 patients (including 10 patients with NSCLC and 4 patients with CRC), of which 12 patients had undergone at least one on-treatment tumor assessment (including 6 patients with NSCLC and 4 patients with CRC), were reported recently. Most patients had received 3 or more prior anti-cancer regimens before study entry (12 of 17 patients, 71%). The following treatment-related adverse events were reported in >10% of patients: diarrhea, nausea, AST increased, vomiting, fatigue, ALT increased, creatinine increased, abdominal distension, abdominal pain, ALP increased, anemia, decreased appetite, dehydration, dry mouth, dysgeusia, dyspnea, QT prolonged, hypomagnesemia, and rash. Grade 3 events included fatigue, decreased appetite, and dyspnea (1 patient each). Anti-tumor activity with PR was achieved in 3 of 6 patients with NSCLC and 1 of 4 patients with CRC across all dose levels evaluated (Jänne et al. AACR-NCI-EORTC International Conference on Molecular Targets and Cancer Therapeutics October 2019).

Compound 1. The specificity of Compound 1 for $KRAS^{G12C}$, together with its mechanism of action, leads to potent and irreversible inhibition of $KRAS^{G12C}$, and is expected to enable a broad therapeutic index, maximizing anti-tumor activity while minimizing treatment-related toxicities. Specific therapies aimed at $KRAS^{G12C}$-positive cancer may provide more tolerable and effective treatment options for patients with advanced stage cancers that harbor $KRAS^{G12C}$. As used within this example, Compound 1 refers to the adipate salt of Compound 1 as described herein unless otherwise specified.

One strategy to improve upon the efficacy of $KRAS^{G12C}$ inhibitors focuses on growing evidence that KRAS inhibition can promote T-cell infiltration and modulate the tumor microenvironment to promote cancer cell killing (Canon et al. Nature 2019; 575:217-23). Thus, this approach aims to combine $KRAS^{G12C}$ inhibitors with other anti-cancer therapies that target critical events along the cancer immunity cycle (Chen and Mellman, Immunity 2013; 39:1-10) in order to collectively enhance the anti-cancer immune response.

In vitro and in vivo pharmacology studies demonstrate that Compound 1 is a highly potent and selective covalent inhibitor of $KRAS^{G12C}$, exhibiting over 20,000-fold selectivity in growth inhibition for $KRAS^{G12C}$-positive over $KRAS^{G12C}$-negative cancer cell lines. Mechanism of action studies with Compound 1 demonstrate that downstream MAPK pathway components such as phosphorylated (p)ERK and pS6, in addition to KRAS target genes such as DUSP6 and SPRY4, are inhibited and apoptosis induction is observed in $KRAS^{G12C}$-positive cancer cell lines. In addition, Compound 1 has potent single-agent activity and inhibits tumor growth in a number of nonclinical xenograft models of $KRAS^{G12C}$-positive lung tumors. These in vitro and in vivo pharmacology studies support the use of Compound 1 for the treatment of patients with locally advanced or metastatic $KRAS^{G12C}$-positive solid tumors.

The results of nonclinical toxicology studies completed to date provide a robust characterization of the toxicity profile of Compound 1 and support the administration of Compound 1 in patients with cancer. Comprehensive nonclinical toxicity studies were completed to evaluate the potential single and repeat dose oral toxicity, genetic toxicity, phototoxicity, and safety pharmacology of Compound 1. Because the $KRAS^{G12C}$ mutation is not present in healthy animals, there are no pharmacologically relevant nonclinical species for $KRAS^{G12C}$ inhibition.

Atezolizumab. Atezolizumab is a humanized IgG1 monoclonal antibody that targets PD-L1 and inhibits the interaction between PD-L1 and its receptors, PD-1 and B7-1 (also known as CD80), both of which function as inhibitory receptors expressed on T cells. Therapeutic blockade of PD-L1 binding by atezolizumab has been shown to enhance the magnitude and quality of tumor-specific T-cell responses, resulting in improved anti-tumor activity (Fehrenbacher et al. 2016; Rosenberg et al. 2016). Atezolizumab has minimal binding to Fc receptors, thus eliminating detectable Fc effector function and associated antibody-mediated clearance of activated effector T cells.

Atezolizumab shows anti-tumor activity in both nonclinical models and cancer patients and is being investigated as a potential therapy in a wide variety of malignancies. Atezolizumab is being studied as a single agent in the advanced cancer and adjuvant therapy settings, as well as in combination with chemotherapy, targeted therapy, and cancer immunotherapy.

Atezolizumab is approved (as a single agent and/or in combination with other anti-cancer therapies) for the treatment of locally advanced or metastatic urothelial carcinoma, NSCLC, small-cell lung cancer, triple-negative breast cancer, melanoma, and hepatocellular carcinoma.

Rationale for Combination Therapy with Atezolizumab. Clinical data emerging in the field of tumor immunotherapy have demonstrated that therapies focused on enhancing T-cell responses against cancer can result in a significant survival benefit in patients with metastatic cancer, including NSCLC (Chen and Mellman 2013; Sun et al. 2020). In metastatic NSCLC, PD-L1/PD-1 inhibitors as monotherapy and/or in combination with chemotherapy have demonstrated significant improvement in survival compared with standard chemotherapy, which has led to the approvals of these agents for the treatment of NSCLC and validates the inhibition of the PD-L1/PD-1 pathway for achieving clinical benefit in NSCLC (Borghaei et al. New Eng J Med 2015; 373:1627-39; Herbst et al.; Reck et al. N Eng J Med 2016; 375:1823-33; Rittmeyer et al. Lancet 2017; 389:255-65; Gandhi et al. New Eng J Med 2018; 31; 378:2078-92; Socinski et al. New Eng J Med 2018; 378:2288-301; West et al. Lancet Oncol 2019; 20:924-37). Furthermore, the safety profile of PD-L1 and PD-1 inhibitors appears to be more tolerable than many chemotherapy combinations, which are associated with substantial toxicities and are often poorly tolerated by the elderly and patients with poor performance status.

One potential obstacle to effective immunotherapy against advanced cancers can be immunosuppressive microenvironments in the tumor. There is evidence that mutant KRAS activity may play a role in promoting an immunosuppressive microenvironment (Cullis et al. Cold Spring Harb Perspect Med 2018; 8:a031849) and that inhibiting mutant KRAS activity may help to modulate the immune microenvironment.

Based on mechanistic and efficacy data from nonclinical models, Compound 1 will be administered in combination with atezolizumab in patients with advanced or metastatic $KRAS^{G12C}$-positive NSCLC. The dose of atezolizumab in combination with Compound 1 will be 1200 mg IV on Day 1 of each 21-day cycle Compound 1 is an oral, covalent, anti-cancer therapeutic agent that selectively inhibits $KRAS^{G12C}$, but not other mutations in KRAS, the wild-type form of KRAS, or other members of the RAS family. Nonclinical studies demonstrate that treatment of $KRAS^{G12C}$-positive cancer cell lines or tumor xenograft models with Compound 1 results in decreased KRAS pathway signaling, suppression of proliferation, and induction of apoptosis.

This study will assess the activity of Compound 1 in combination with atezolizumab on the basis of the following endpoints: Objective response rate (ORR); Duration of response (DOR); and Progression-free survival (PFS).

Biomarkers. This study will identify and/or evaluate biomarkers that are predictive of response to Compound 1 as a single agent or in combination with atezolizumab (i.e., predictive biomarkers), early surrogates of activity, associated with progression to a more severe disease state (i.e., prognostic biomarkers), associated with acquired resistance to $KRAS^{G12C}$ inhibitors (e.g., Compound 1), associated with susceptibility to developing adverse events or can lead to improved adverse event monitoring or investigation (i.e., safety biomarkers), can provide evidence of Compound 1 activity in combination with atezolizumab (i.e., pharmacodynamic [PD] biomarkers), or can increase the knowledge and understanding of disease biology and drug safety. Corresponding biomarker endpoints include the relationship between exploratory biomarkers in blood, plasma, and tumor tissue and safety, PK, activity, or other biomarker endpoints.

Study Parameters. Patients who do not meet the criteria for participation in this study (screen failure) may qualify for up to two re-screening opportunities (for a total of three screenings per participant) at the investigator's discretion. Patients are not required to re-sign the consent form if they are re-screened within 30 days after previously signing the consent form. For patients who are re-screened, all eligibility criteria must be re-evaluated and screening assessments should be repeated as applicable to meet the eligibility criteria described herein.

The study consists of a screening period of up to 28 days, a treatment period, and a safety follow-up period during which patients will be followed for safety outcomes for a treatment-specific period after their final dose of study drug or until they receive another anti-cancer therapy, whichever occurs first. Patients who provide a separate consent may be screened for $KRas^{G12C}$ mutation status through central testing of circulating tumor DNA (ctDNA).

In the absence of unacceptable toxicities and unequivocal disease progression as determined by the investigator, patients may continue treatment with Compound 1 until the end of the study.

All patients will be closely monitored for adverse events throughout the study and for a treatment-specific period after the final dose of study treatment or until initiation of another anti-cancer therapy, whichever occurs first. Adverse events will be graded according to the NCI CTCAE v5.0.

The starting dose of Compound 1 will be 50 mg PO QD. Single-patient dose-escalation cohorts will be treated at escalating dose levels of Compound 1.

Patients include those with locally advanced, recurrent, or metastatic incurable $KRas^{G12C}$-positive NSCLC who have disease progression or intolerance to at least one prior systemic therapy that may include single-agent or combination therapy with an investigational or approved PD-L1/PD-1 inhibitor.

$KRas^{G12C}$ Mutation Status from Tissue and Circulating Tumor DNA Assessments. Approximately 12% of NSCLC, 4% of CRC, 2% of pancreatic cancers, and many other solid tumors (prevalence 4% in each) harbor the KRas$^{G12C}$ mutation. Compound 1 is a potent and highly selective inhibitor that targets KRas$^{G12C}$, but not other mutations in KRAS, the wild-type form of KRAS, or other members of the RAS family. Therefore, only patients with tumors harboring the KRas$^{G12C}$ mutation are eligible for administration of combination therapies described herein. KRAS mutation status may be determined using the FoundationOne® CDx (F1CDx) assay, a U.S. Food and Drug Administration (FDA)-approved broad companion diagnostic (CDx) assay, FoundationOne® Liquid CDx (F1L CDx) assay, as well as other FDA approved (FDA 2020) or well-validated laboratory developed tests performed in a Clinical Laboratory Improvement Amendments (CLIA)-validated or equivalently certified laboratory. Previous studies indicate that occurrence of the KRas$^{G12C}$ mutation is an early event (Jamal-Hanjani et al. N Engl J Med 2017; 376:2109-21), suggesting that analysis of archival tissue is a sufficient surrogate for selection of patients with KRas$^{G12C}$-positive tumors for Compound 1 treatment.

Pharmacodynamic Pathway Modulation. Compound 1 is a KRas$^{G12C}$ inhibitor that suppresses downstream MAPK signaling by alkylation of KRas$^{G12C}$, thereby locking it in its inactive GDP-bound state. In nonclinical models, the level of KRas$^{G12C}$ alkylation by Compound 1 and the extent of MAPK pathway suppression correlate with response to Compound 1. Pre-treatment and on-treatment tumor tissue collection will enable an assessment of the correlation of MAPK pathway suppression and anti-tumor activity with Compound 1 treatment. The extent of MAPK pathway suppression can be assessed using RNA analysis of MAPK target genes (e.g., DUSP6, SPRY4) or immunohistochemistry (IHC) analysis of phosphorylated downstream markers (e.g., pERK, pS6). In addition, on-treatment tumor tissue biopsies may enable direct assessment of the level of KRas$^{G12C}$ alkylation by Compound 1. The assessment of these PD biomarkers may inform future dose selection.

Sequencing of Genes Related to Resistance to Compound 1. DNA sequencing techniques, such as targeted next-generation sequencing (NGS) and whole exome sequencing, may offer a unique opportunity to identify biomarkers of response and/or resistance to Compound 1. Sequencing of cancer-related genes may result in the identification of de novo and acquired mechanisms of resistance to Compound 1.

Protein, RNA, and DNA Analysis. Evaluation of the signaling activities (e.g., MAPK, PI3K/AKT) in tumor cells and the immune activities (e.g., PD-L1) in the tumor microenvironment could provide valuable insights in the sensitivity or resistance to Compound 1 treatment as a single agent or in combination therapy. PD-L1 expression assessed by IHC may be performed for the analysis of anti-tumor activity in subgroups based on PD-L1 expression.

In addition to mutational activation of proteins, expression levels of RNA or alterations in DNA may also modulate the activity of signaling pathways. RNA profiling of tumors will allow intrinsic subtyping of patients enrolled in the study. Analysis of the potential association between subtypes and patient outcome may identify subpopulations of patients who are most likely to respond to Compound 1.

Plasma Sample for Somatic Tumor Mutation Analysis and Other Biomarkers. There is increasing evidence that cell-free DNA obtained from blood specimens of patients with cancer contains ctDNA, which is representative of the DNA and mutational status of cells in the tumor (Diehl et al. 2008; Maheswaran et al. 2008). Assays have been validated to detect cancer-related mutations (e.g., KRAS) from plasma. Results of these assays may be correlated with the mutational status determined from analysis of tumor specimens. The use of ctDNA to monitor response to treatment is an area of great interest, and could allow for an early, non-invasive, and quantifiable method for use in the clinical setting to identify candidates for specific therapies and monitoring of mutation status of the cancer over time (Wan et al. Nat Rev Cancer 2017; 17:223-38). Analysis of ctDNA collected at various times during study treatment and after a patient progresses on Compound 1 may help to identify mechanisms of response and acquired resistance to study treatment.

Blood Sample for Next-Generation Sequencing. Next-generation sequencing (NGS) technologies can generate a large quantity of sequencing data. Tumor DNA can contain both reported and unreported chromosomal alterations because of the tumorigenesis process. To help control for sequencing calls in previously unreported genomic alterations, a predose blood sample will be taken to determine whether the alteration is somatic.

Optional Tumor Biopsy Sample at the Time of Disease Progression. Understanding the mechanisms of resistance to KRAS$^{G12C}$ inhibitors is critical for the development of combination therapies and may provide an opportunity to develop next-generation inhibitors to prevent resistance. Notable examples include the T790M gatekeeper acquired mutation in EGFR in patients who progress on EGFR inhibitors and reactivation of the MAPK pathway in BRAF-mutant melanoma cancers that progress on BRAF inhibitors.

In all arms, tumor tissue may be collected at the time of disease progression to perform additional exploratory biomarker analyses. These analyses may include, but are not limited to DNA and RNA NGS or protein-based methods to assess cancer-related genes and biomarkers associated with common molecular and biological pathways.

Inclusion Criteria. Patients must meet the following criteria for study entry:
Age 18 years at time of signing Informed Consent Form;
Evaluable or measurable disease per RECIST v1.1;
Eastern Cooperative Oncology Group (ECOG) performance status of 0 or 1;
Life expectancy of ≥12 weeks;
Adequate hematologic and organ function within 14 days prior to initiation of study treatment, defined by the following:
  Absolute neutrophil count ≥1200/μL;
  Hemoglobin ≥9 g/dL;
  Platelet count ≥100,000/μL;
  Total bilirubin ≤1.5×ULN;
  Serum albumin ≥2.5 g/dL;
  AST and ALT ≤2.5×ULN with the following exception: Patients with documented liver metastases may have AST and/or ALT ≤5.0×ULN.
  Serum creatinine ≤1.5×ULN or creatinine clearance ≥50 mL/min on the basis of the Cockcroft-Gault glomerular filtration rate estimation:

(140−age)×(weight in kg)×(0.85 if female)72×(serum creatinine in mg/dL)

For women of childbearing potential: Agreement to remain abstinent (refrain from heterosexual intercourse) or use contraception, and agreement to refrain from donating eggs, as defined below:
For men who are not surgically sterile: Agreement to remain abstinent (refrain from heterosexual intercourse) or use contraception, and agreement to refrain from donating sperm, as defined below:

Confirmation of biomarker eligibility: Valid results from either central testing of blood or local testing of blood or tumor tissue documenting the presence of the $KRas^{G12C}$ mutation (e.g. validated polymerase chain reaction (PCR)-based or NGS assay performed at a CLIA or equivalently certified laboratory).

Additional Inclusion Criteria.

Histologically documented, locally advanced, recurrent, or metastatic incurable NSCLC, without a known concomitant second oncogenic driver (e.g., sensitizing EGFR mutations, ALK rearrangement, ROS1 rearrangement, BRAF V600E mutation, NTRK fusions, RET fusions) as determined by the FMI NGS assay or by a Sponsor-approved validated PCR-based or NGS assay performed at a local CLIA-certified or equivalently-certified laboratory Disease progression or intolerance to at least 1 prior systemic therapy. This may include single-agent or combination therapy with an investigational or approved PD-L1/PD-1 inhibitor.

Lymphocyte count ≥5×109/L (500/µL)

Adequate viral serology within 14 days prior to initiation of study treatment, defined by the following:
Negative HIV test at screening;
Negative hepatitis B surface antigen (HBsAg) test at screening;
Positive hepatitis B surface antibody (HBsAb) test at screening;
Negative hepatitis C virus (HCV) antibody test at screening.

General Exclusion Criteria. Patients who meet any of the following criteria will be excluded:

Inability or unwillingness to swallow pills;
Inability to comply with study and follow-up procedures;
Malabsorption syndrome or other condition that interferes with enteral absorption;
Known and untreated, or active central nervous system (CNS) metastases;
Patients with a history of treated CNS metastases provided they meet all of the following criteria:
Measurable or evaluable disease outside the CNS;
No history of intracranial hemorrhage or spinal cord hemorrhage;
No ongoing requirement for corticosteroids as therapy for CNS metastases, with corticosteroids discontinued for 2 weeks prior to administration of an agent described herein and no ongoing symptoms attributed to CNS metastases;
No stereotactic radiation within 7 days or whole-brain radiation within 14 days prior to Day 1 of Cycle 1;
No evidence of interim progression between the completion of CNS-directed therapy and the screening radiographic study;
Leptomeningeal disease or carcinomatous meningitis;
Uncontrolled pleural effusion, pericardial effusion, or ascites requiring recurrent drainage procedures biweekly or more frequently;
Indwelling pleural or abdominal catheters may be allowed, provided the patient has adequately recovered from the procedure, is hemodynamically stable and symptomatically improved;
Any active infection that could impact patient safety, or serious infection requiring IV antibiotics within 7 days prior to Day 1 of Cycle 1;
Clinically significant history of liver disease, including viral or other hepatitis, current alcohol abuse, or cirrhosis;
Known HIV infection;
Uncontrolled hypercalcemia (>1.5 mmol/L ionized calcium or calcium >12 mg/dL or corrected serum calcium ULN) or symptomatic hypercalcemia requiring continued use of bisphosphonate therapy or denosumab;
Significant traumatic injury or major surgical procedure within 4 weeks prior to Day 1 of Cycle 1;
Patients with chronic diarrhea, short bowel syndrome or significant upper gastrointestinal surgery including gastric resection, a history of inflammatory bowel disease (e.g., Crohn's disease or ulcerative colitis) or any active bowel inflammation (including diverticulitis);
Prior treatment with any $KRAS^{G12C}$ inhibitor
Treatment with chemotherapy, immunotherapy, or biologic therapy as anti-cancer therapy within 3 weeks prior to administration of an agent described herein, or endocrine therapy within 2 weeks prior administration of an agent described herein, except for the following:
Hormonal therapy with gonadotropin-releasing hormone (GnRH) agonists or antagonists for endocrine sensitive cancers (e.g., prostate, endometrial, hormone receptor-positive breast cancer);
Kinase inhibitors, approved by regulatory authorities, may be used up to 2 weeks prior to initiation of study treatment;
Treatment with an investigational agent within 3 weeks or five half-lives prior to administration of an agent described herein, whichever is shorter.
Radiation therapy (other than palliative radiation to bony metastases and radiation to CNS metastases) as cancer therapy within 4 weeks prior to administration of an agent described herein;
Palliative radiation to bony metastases within 2 weeks prior to administration of Compound 1;
Adverse events from prior anti-cancer therapy that have not resolved;
History of other malignancy within 5 years prior to screening;
History of or active clinically significant cardiovascular dysfunction, including:
History of stroke or transient ischemic attack within 6 months prior to administration of an agent described herein;
History of myocardial infarction within 6 months prior to administration of an agent described herein;
New York Heart Association Class III or IV cardiac disease or congestive heart failure requiring medication
Uncontrolled arrhythmias, history of or active ventricular arrhythmia requiring medication;
Coronary heart disease that is symptomatic or unstable angina;
Congenital long QT syndrome or QT interval corrected through use of Fridericia's formula (QTcF) >470 ms;
Current treatment with medications known to prolong the QT interval;
Pregnant or breastfeeding, or intending to become pregnant during the study or within 6 months after the final dose of Compound 1;
Active or history of autoimmune disease or immune deficiency, including, but not limited to, myasthenia gravis, myositis, autoimmune hepatitis, myocarditis, systemic lupus erythematosus, rheumatoid arthritis, inflammatory bowel disease, antiphospholipid antibody syndrome, Wegener granulomatosis, Sjögren syndrome, Guillain-Barré syndrome, or multiple sclerosis, with the following exceptions:
Patients with a history of autoimmune-related hypothyroidism who are on thyroid-replacement hormone;
Patients with controlled Type 1 diabetes mellitus who are on an insulin regimen;
Patients with eczema, psoriasis, lichen simplex chronicus, or vitiligo with dermatologic manifestations only provided all of following conditions are met:
Rash must cover <10% of body surface area;
Disease is well controlled on Day 1 and requires only low-potency topical corticosteroids;
No occurrence of acute exacerbations of the underlying condition requiring psoralen plus ultraviolet A radiation, methotrexate, retinoids, biologic pulmonary disease (COPD) or asthma, or low-dose corticosteroids for orthostatic hypotension or adrenal insufficiency Patients with any history of immune deficiencies or autoimmune disease listed in the table below are excluded from participating in the study. Possible exceptions to this exclusion could be patients with a medical history of such entities as atopic disease or childhood arthralgias, where the clinical suspicion of autoimmune disease is low. Patients with a history of autoimmune-related hypothyroidism on a stable dose of thyroid replacement hormone may be eligible for this study. In addition, transient autoimmune manifestations of an acute infectious disease that resolved upon treatment of the infectious agent are not excluded (e.g., acute Lyme arthritis).

| Autoimmune Diseases and Immune Deficiencies | | |
|---|---|---|
| Acute disseminated encephalomyelitis | Epidermolysis bullosa acquista | Ord's thyroiditis |
| Addison's disease | Gestational pemphigoid | Pemphigus |
| ANKA positive vasculitis | Giant cell arteritis | Pernicious anemia |
| Ankylosing spondylitis | Glomerulonephritis | Polyarteritis nodusa |
| Antiphospholipid antibody syndrome | Goodpasture's syndrome | Polyarthritis |
| Aplastic anemia | Graves' disease | Polychondritis |
| Autoimmune hemolytic anemia | Guillain-Barré syndrome | Polyglandular autoimmune |
| Autoimmune hepatitis | Hashimoto's disease | Polymyositis |
| Autoimmune hypoparathyroidism | IgA nephropathy | Primary biliary cirrhosis |
| Autoimmune hypophysitis | Inflammatory bowel disease | Psoriasis |
| Autoimmune myocarditis | Interstitial cystitis | Reiter's syndrome |
| Autoimmune oophoritis | Kawasaki's disease | Pyoderma gangrenosum |
| Autoimmune orchitis | Lambert-Eaton myasthenia syndrome | Reactive arthritis |
| Autoimmune thrombocytopenic purpura | Lupus erythematosus | Rheumatoid arthritis |
| Behcet's disease | Lyme disease - chronic | Sarcoidosis |
| Bullous pemphigoid | Meniere's syndrome | Scleroderma |
| Celiac disease | Mixed connective tissue disease | Sjögren's syndrome |
| Chronic fatigue syndrome | Mooren's ulcer | Stiff-Person syndrome |
| Chronic inflammatory demyelinating polyneuropathy | Morphea | Takayasu's arteritis |
| Chung-Strauss syndrome | Multiple sclerosis | Ulcerative colitis |
| Crohn's disease | Myasthenia gravis | Vitiligo |
| Dermatomyositis | Neuromyotonia | Vogt-Kovanagi-Harada disease |
| Diabetes mellitus type 1 | Opsoclonus myoclonus syndrome | Wegener's granulomatosis |
| Dysautonomia | Optic neuritis | | agents, oral calcineurin inhibitors, or high-potency or oral corticosteroids within the previous 12 months;
History of idiopathic pulmonary fibrosis, organizing pneumonia (e.g., bronchiolitis obliterans), drug-induced pneumonitis, or idiopathic pneumonitis, or evidence of active pneumonitis;
Treatment with systemic immunosuppressive medication (including, but not limited to, corticosteroids, cyclophosphamide, azathioprine, methotrexate, thalidomide, and anti-TNF-α agents) within 4 weeks or 5 drug-elimination half-lives (whichever is longer) prior to first dose and during treatment with atezolizumab, with the following exceptions:
Patients who received acute, low-dose systemic immunosuppressant medication or a one-time pulse dose of systemic immunosuppressant medication (e.g., 48 hours of corticosteroids for a contrast allergy);
Patients who received mineralocorticoids (e.g., fludrocortisone), corticosteroids for chronic obstructive Study Treatment Formulation, Packaging, and Handling.
Compound 1. Compound 1 will be supplied as an active pharmaceutical ingredient (API) powder-in-capsule (PIC) formulation in three strengths: 5 mg, 25 mg, and 100 mg (free base equivalent). Additionally, a film-coated tablet formulation in a dose strength of 100 mg (free base equivalent) will also be supplied for clinical use. Compound 1 drug products should be stored at or below 86° F. (30° C.) and protected from moisture.

For Compound 1 doses to be administered at home, a sufficient number of capsules or tablets should be dispensed to the patient to last until the next visit or through one cycle. Patients will self-administer Compound 1 as provided herein, except when patients visit a clinic. Patients should take Compound 1 at approximately the same time each day unless otherwise instructed. Patients will be instructed as to the number and strength of capsules or tablets to take, according to their assigned dose level and schedule.

Unless otherwise instructed, Compound 1 should be taken on an empty stomach, i.e., food should be avoided at least 2 hours before as well as 1 hour after the dose is administered. There are no restrictions on water intake. Importantly, Compound 1 capsules or tablets will be swallowed whole (not chewed) with a minimum of 240 mL (8 fluid ounces) of water. If a patient misses any dose of Compound 1 or vomits up a capsule or tablet, the patient should be instructed to skip that dose and resume dosing with the next scheduled dose. Missed doses will not be made up.

Atezolizumab. Atezolizumab will be supplied as an IV formulation in 1200 mg/20 mL vials. Atezolizumab will be administered by IV infusion at a fixed dose of 1200 mg on Day 1 of each 21-day cycle, following administration of Compound 1. The start of the atezolizumab administration should be about 30 minutes after the oral administration of Compound 1. Administration of atezolizumab will be performed in a monitored setting where there is immediate access to trained personnel and adequate equipment and medicine to manage potentially serious reactions. Atezolizumab infusions will be administered per the instructions outlined in Table 1 herein. No dose modification for atezolizumab is allowed.

In the event atezolizumab administration is held due to an adverse event in a given cycle, the next dosing cycle should not begin until administration of atezolizumab can be resumed. As such, the current cycle may be extended past 21 days, and the patient may continue to receive Compound 1. Day 1 of the next cycle should correspond to the timepoint at which administration of atezolizumab is resumed.

Concomitant Therapy. Concomitant therapy consists of any medication (e.g. prescription drugs, over-the-counter drugs, vaccines, herbal or homeopathic remedies, nutritional supplements) used by a patient in addition to an agent described herein from 7 days prior to the first administration of at least one agent described herein to the last administration of at least one agent described herein.

Permitted Therapy. Patients may take (a) anti-seizure medications or warfarin; (b) oral contraceptives or other allowed maintenance therapy as specified in the eligibility criteria; (c) anti-emetics and anti-diarrheal medications should not be administered prophylactically before initial treatment with study drug; (d) pain medications; (e) bisphosphonate and denosumab therapy for bone metastases or osteopenia or osteoporosis; or multivitamins, calcium, and vitamins C, D, and E supplements are allowed.

Precautionary Therapy. Medications Given with Precaution due to Effects Related to CYP Enzymes and Compound 1 include, for example, (1) Strong/moderate CYP3A4 inhibitors, including, but not limited to, the following: atazanavir, ritonavir, indinavir, nelfinavir, saquinavir, clarithromycin, telithromycin, erythromycin, troleandomycin, fluconazole, itraconazole, ketoconazole, voriconazole, posaconazole, aprepitant, conivaptan, fluvoxamine, diltiazem, nefazodone, mibefradil, verapamil, and grapefruit juice or grapefruit supplements; (2) Strong/moderate CYP3A4 inducers, including, but not limited to, the following: rifampin, carbamazepine, phenytoin, oxcarbazepine, phenobarbital, efavirenz, nevirapine, etravirine, modafinil, hyperforin (St. John's Wort), and cyproterone. The use of full-dose oral or parenteral anticoagulants for therapeutic purpose as long as the INR and/or aPTT is within therapeutic limits (according to institution standards) within 14 days prior to administration of any agent described herein and the patient has been on a stable dose of anticoagulants for 1 week prior to initiation of study treatment. The lists of medications are not intended to be comprehensive.

Other Medications Given with Precaution. Systemic corticosteroids, immunosuppressive medications, and TNF-α inhibitors.

Prohibited Therapy. Use of the following concomitant therapies is prohibited during and for at least 7 days prior to the first administration of an agent described herein:
  Investigational therapy within 3 weeks or five half-lives prior to the first administration of an agent described herein, whichever is shorter;
  Concomitant therapy intended for the treatment of cancer whether approved by the FDA or experimental, including chemotherapy, radiotherapy, immunotherapy, biologic therapy, herbal therapy, or hormonal therapy except for the following:
    Hormonal therapy with gonadotropin-releasing hormone (GnRH) agonists or antagonists for endocrine sensitive cancers (e.g. prostate, endometrial, hormone receptor-positive breast cancer);
    Hormone replacement therapy or oral contraception.
  Radiotherapy for unequivocal progressive disease with the exception of new brain metastases in the setting of systemic response: patients who have demonstrated control of their systemic disease (defined as having received clinical benefit [i.e., a PR, CR, or SD for months]), but who have developed brain metastases that are treatable with radiation, will be allowed to continue to receive therapy with Compound 1 during the study until they either experience systemic progression of their disease and/or further progression in the brain (based on investigator assessments);
  Quinidine or other anti-arrhythmic agents;
  Initiation or increased dose of hematopoietic colony-stimulating factors (CSFs; e.g., granulocyte CSF; filgrastim, granulocyte/macrophage CSF; sargramostim, pegfilgrastim, erythropoietin, darbepoetin, and thrombopoietin) from 7 days before Cycle 1, Day 1
  Live, attenuated vaccines (e.g., FluMist®) within 4 weeks prior to the first administration of an agent described herein, during atezolizumab treatment, and for 5 months after the final dose of atezolizumab;
  Systemic immunostimulatory agents (including, but not limited to, interferons and IL 2) within 4 weeks or 5 drug-elimination half-lives (whichever is longer) prior to the first administration of an agent described herein and during study treatment.

Risks Associated with Compound 1. Administration of Compound 1 has been associated diarrhea, nausea, vomiting, oral mucosal irritation, minimal to mild transaminase elevation, and phototoxicity.

Risks Associated with Atezolizumab. Atezolizumab has been associated with risks such as the following: infusion related reactions (IRRs) and immune-mediated hepatitis, pneumonitis, colitis, pancreatitis, diabetes mellitus, hypothyroidism, hyperthyroidism, adrenal insufficiency, hypophysitis, Guillain-Barré syndrome, myasthenic syndrome or myasthenia gravis, meningoencephalitis, myocarditis, nephritis, and myositis. Immune-mediated reactions may involve any organ system and may lead to hemophagocytic lymphohistiocytosis (HLH) and macrophage activation syndrome (MAS).

Although most immune-mediated adverse events observed with immunomodulatory agents have been mild and self-limiting, such events should be recognized early and treated promptly to avoid potential major complications (Di Giacomo et al. 2010). Potential overlapping toxicities associated with combination use of atezolizumab and Compound 1 are gastrointestinal toxicities and elevated hepatic transaminases.

Treatment Interruption. If Compound 1 is held for >21 days from the previous study treatment due to toxicity, the study treatment should not be re-initiated. Compound 1 may be suspended for up to 21 days for unanticipated intercurrent medical events that are not associated with study treatment toxicity or disease progression.

Adverse Events. An adverse event as defined herein refers to any untoward medical occurrence in a clinical investigation subject administered an agent described herein in the combination therapies described herein, regardless of causal attribution. The terms "severe" and "serious" are not synonymous. Severity refers to the intensity of an adverse event (e.g., rated as mild, moderate, or severe, or according to NCI CTCAE); the event itself may be of relatively minor medical significance (such as severe headache without any further findings).

Adverse events to be monitored include nausea, vomiting, diarrhea, stomatitis, mucositis, hepatitis or elevation in ALT or AST, elevated bilirubin or clinical jaundice, systemic lupus erythematosus, nephritis, Events suggestive of hypersensitivity, infusion-mediated reactions, cytokine release syndrome (CRS), influenza-like illness, and hemophagocytic lymphohistiocytosis (HLH), macrophage activation syndrome (MAS), atrial fibrillation, myocarditis, pericarditis, Vasculitis, Myositis, uveitis, retinitis, optic neuritis, autoimmune hemolytic anemia, Stevens-Johnson syndrome, dermatitis bullous, and toxic epidermal necrolysis.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

Where a range of values is provided, it is understood that each intervening value, to the tenth of the unit of the lower limit, unless the context clearly dictates otherwise, between the upper and lower limit of the range and any other stated or intervening value in that stated range, is encompassed herein. The upper and lower limits of these small ranges which can independently be included in the smaller rangers is also encompassed herein, subject to any specifically excluded limit in the stated range. Where the stated range includes one or both of the limits, ranges excluding either or both of those included limits are also included herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of treating lung cancer comprising a KRas$^{G12C}$ mutation in a patient having such a lung cancer, the method comprising administering an effective amount of a combination therapy comprising:
   (a) Compound 1

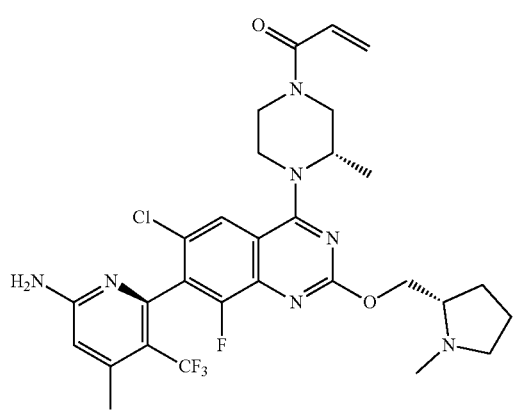

(1)

or an adipate salt thereof orally as a tablet or capsule QD at an amount of 200 mg or 400 mg on days 1-21 of a first 21-day cycle and;
   (b) atezolizumab administered an amount of about 1200 mg Q3W on day 1 of the first 21-day cycle.

2. The method of claim 1, wherein the lung cancer is non-small cell lung cancer (NSCLC).

3. The method of claim 1, wherein the lung cancer is adenocarcinoma, squamous-cell lung carcinoma or large-cell lung carcinoma.

4. The method of claim 1, wherein atezolizumab is administered after administration of Compound 1 or a pharmaceutically acceptable salt thereof.

5. A method of treating non-small cell lung cancer (NSCLC) comprising a KRas$^{G12C}$ mutation in a patient having such NSCLC, the method comprising administering to the patient a treatment regimen comprising:
   (i) the adipate salt of Compound 1

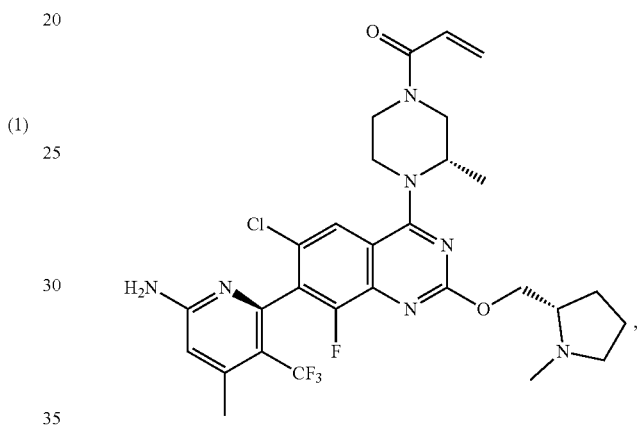

at an amount of about 400 mg QD on days 1-21 of a first 21-day cycle; and
   (ii) atezolizumab Q3W at an amount of 1200 mg on day 1 of the first 21-day cycle.

6. The method of claim 1, further comprising two or more cycles and a rest period of 7 days between the cycles.

7. The method of claim 5, further comprising two or more cycles and a rest period of 7 days between the cycles.

8. The method of claim 1, wherein the adipate salt of Compound 1 is administered at an amount of about 200 mg.

9. The method of claim 1, wherein the adipate salt of Compound 1 is administered at an amount of about 400 mg.

10. The method of claim 1, wherein the patient has not been previously treated with a KRas G12C inhibitor.

11. The method of claim 1, wherein the patient has previously treated with a KRas G12C inhibitor.

12. The method of claim 5, wherein the patient has not been previously treated with a KRas G12C inhibitor.

13. The method of claim 5, wherein the patient has previously treated with a KRas G12C inhibitor.

* * * * *

SEQUENCE LISTING

```
<160> NUMBER OF SEQ ID NOS: 10

<210> SEQ ID NO 1
<211> LENGTH: 447
<212> TYPE: PRT
<213> ORGANISM: Artificial Sequence
<220> FEATURE:
<223> OTHER INFORMATION: Synthetic Construct

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

```
Ser Gly Ala Leu Thr Ser Gly Val His Thr Phe Pro Ala Val Leu Gln
            165                 170                 175

Ser Ser Gly Leu Tyr Ser Leu Ser Val Val Thr Val Pro Ser Ser
        180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 2
<211> LENGTH: 214
<212> TYPE: PRT
<213> ORGANISM: Artificial Sequence
<220> FEATURE:
<223> OTHER INFORMATION: Synthetic Construct

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Gly Phe Thr Phe Ser Asp Ser Trp Ile His
1               5                   10

<210> SEQ ID NO 4
<211> LENGTH: 18
<212> TYPE: PRT
<213> ORGANISM: Artificial Sequence
<220> FEATURE:
<223> OTHER INFORMATION: Synthetic Construct

<400> SEQUENCE: 4

Ala Trp Ile Ser Pro Tyr Gly Gly Ser Thr Tyr Tyr Ala Asp Ser Val
1               5                   10                  15

Lys Gly

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct

<400> SEQUENCE: 5

Arg His Trp Pro Gly Gly Phe Asp Tyr
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic Construct

<400> SEQUENCE: 6

Arg Ala Ser Gln Asp Val Ser Thr Ala Val Ala
```

<210> SEQ ID NO 7
<211> LENGTH: 7
<212> TYPE: PRT
<213> ORGANISM: Artificial Sequence
<220> FEATURE:
<223> OTHER INFORMATION: Synthetic Construct

<400> SEQUENCE: 7

Ser Ala Ser Phe Leu Tyr Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

Gln Gln Tyr Leu Tyr His Pro Ala Thr
1               5

<210> SEQ ID NO 9
<211> LENGTH: 118
<212> TYPE: PRT
<213> ORGANISM: Artificial Sequence
<220> FEATURE:
<223> OTHER INFORMATION: Synthetic Construct

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 10
<211> LENGTH: 108
<212> TYPE: PRT
<213> ORGANISM: Artificial Sequence
<220> FEATURE:
<223> OTHER INFORMATION: Synthetic Construct

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile

```
                35                  40                  45
Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105
```